(12) United States Patent
Banet et al.

(10) Patent No.: US 9,554,719 B2
(45) Date of Patent: Jan. 31, 2017

(54) INTERNET-BASED SYSTEM FOR EVALUATING T WAVES WITHIN ECG WAVEFORMS TO DETERMINE THE PRESENCE OF CARDIAC ABNORMALITIES

(71) Applicant: TOSENSE, INC., La Jolla, CA (US)

(72) Inventors: Matthew Banet, San Diego, CA (US); Gregory Kent Feld, Rancho Santa Fe, CA (US); Marshal Singh Dillon, San Diego, CA (US); Adolfo Meza-Guinea, Chula Vista, CA (US); Susan Meeks Pede, Encinitas, CA (US); Andrew Terry, San Diego, CA (US)

(73) Assignee: TOSENSE, INC., San Diego, CA (US)

( * ) Notice: Subject to any disclaimer, the term of this patent is extended or adjusted under 35 U.S.C. 154(b) by 24 days.

(21) Appl. No.: 14/048,723

(22) Filed: Oct. 8, 2013

(65) Prior Publication Data

US 2015/0005650 A1    Jan. 1, 2015

Related U.S. Application Data

(60) Provisional application No. 61/711,084, filed on Oct. 8, 2012.

(51) Int. Cl.
*A61B 5/04* (2006.01)
*A61B 5/0452* (2006.01)
(Continued)

(52) U.S. Cl.
CPC .......... *A61B 5/0452* (2013.01); *A61B 5/0006* (2013.01); *A61B 5/0022* (2013.01); *A61B 5/046* (2013.01); *A61B 5/0464* (2013.01); *A61B 5/0468* (2013.01)

(58) Field of Classification Search
CPC .. A61B 5/04021; A61B 5/0468; A61N 1/3621
See application file for complete search history.

(56) References Cited

U.S. PATENT DOCUMENTS

| | | | |
|---|---|---|---|
| 6,440,066 B1 * | 8/2002 | Bardy ................. | A61B 5/0002 128/923 |
| 7,751,875 B2 | 7/2010 | Bojovic et al. | |

(Continued)

*Primary Examiner* — Christopher D Koharski
*Assistant Examiner* — Natasha Patel
(74) *Attorney, Agent, or Firm* — Acuity Law Group, PC; Michael A. Whittaker

(57) ABSTRACT

The present invention provides an improved, Internet-based system that seamlessly collects cardiovascular data from a patient before, during, and after a procedure for EP or an ID. During an EP procedure, the system collects information describing the patient's response to PES and the ablation process, ECG waveforms and their various features, HR and other vital signs, HR variability, cardiac arrhythmias, patient demographics, and patient outcomes. Once these data are collected, the system stores them on an Internet-accessible computer system that can deploy a collection of user-selected and custom-developed algorithms. Before and after the procedure, the system also integrates with body-worn and/or programmers that interrogate implanted devices to collect similar data while the patient is either ambulatory, or in a clinic associated with the hospital. A data-collection/storage module, featuring database interface, stores physiological and procedural information measured from the patient.

15 Claims, 18 Drawing Sheets

(51) Int. Cl.
*A61B 5/00* (2006.01)
*A61B 5/046* (2006.01)
*A61B 5/0464* (2006.01)
*A61B 5/0468* (2006.01)

(56) References Cited

U.S. PATENT DOCUMENTS

| | | | |
|---|---|---|---|
| 2005/0027202 A1* | 2/2005 | Ginzburg | A61B 5/044 |
| | | | 600/509 |
| 2006/0013456 A1* | 1/2006 | Soykan | G06F 19/24 |
| | | | 382/128 |
| 2006/0167365 A1* | 7/2006 | Bharmi | 600/517 |
| 2010/0042172 A1* | 2/2010 | Armoundas | 607/17 |
| 2012/0123232 A1* | 5/2012 | Najarian | A61B 5/0022 |
| | | | 600/345 |

* cited by examiner

| Patient ID | Gender | Date of Birth | Weight | Height | ICD? |
|---|---|---|---|---|---|
| 001 | M | 9/13/65 | 190 | 72 | Y |
| 002 | M | 4/02/54 | 156 | 73 | N |
| 003 | F | 5/08/78 | 98 | 61 | Y |
| 004 | M | 6/25/56 | 220 | 74 | Y |
| 005 | F | 7/12/67 | 155 | 66 | N |
| 006 | M | 9/20/72 | 130 | 62 | N |
| 007 | M | 1/23/45 | 195 | 73 | N |
| 008 | M | 6/06/56 | 187 | 69 | N |
| 009 | M | 3/29/80 | 254 | 77 | Y |
| 010 | M | 8/19/71 | 121 | 63 | N |

INTERNET-BASED SYSTEM FOR EVALUATING T WAVES WITHIN ECG WAVEFORMS TO DETERMINE THE PRESENCE OF CARDIAC ABNORMALITIES

CROSS REFERENCES TO RELATED APPLICATIONS

This application claims the benefit of U.S. Provisional Application No. 61/711,084, filed Oct. 8, 2012, which is hereby incorporated in its entirety including all tables, figures, and claims.

STATEMENT REGARDING FEDERALLY SPONSORED RESEARCH OR DEVELOPMENT

None.

BACKGROUND OF THE INVENTION

Field of the Invention

The present invention relates to systems for processing data from patients undergoing cardiovascular procedures, e.g. electrophysiology (EP) procedures.

Description of the Related Art

Patients with abnormal cardiac rhythms can be treated with EP, or receive an implanted device (ID), such as a pacemaker or implantable cardioverter-defibrillator (ICD). These therapies and devices are effective in restoring the patient's cardiac rhythm to a normal level, and are typically characterized by a collection of data-generating devices that are used before, during, and after procedures for EP or the ID.

Prior to such a procedure, physicians often prescribe electrocardiography (ECG) monitors that measure time-dependent waveforms, from which heart rate (HR) and information related to arrhythmias and other cardiac properties are extracted. These systems can characterize ambulatory patients over short periods (e.g. 24-48 hours) using 'holier' monitors, or over longer periods (e.g. 1-3 weeks) using cardiac event monitors. Conventional holter or event monitors typically include a collection of chest-worn ECG electrodes (typically 3 or 5), an ECG circuit that collects analog signals from the ECG electrodes and coverts these into multi-lead ECG waveforms, and a computer processing unit that analyzes the ECG waveforms to determine cardiac information. Typically the patient wears the entire system on their body. Some modern ECG-monitoring systems include wireless capabilities that transmit ECG waveforms and other numerical data through a cellular interface to an Internet-based system, where they are further analyzed to generate, for example, reports describing the patient's cardiac rhythm. In less sophisticated systems, the ECG-monitoring system is worn by the patient, and then returned to a company that downloads all relevant information into a computer, which then analyzes it to generate the report. The report, for example, may be imported into the patient's electronic medical record (EMR). The EMR avails the report to cardiologists or other clinicians, who then use it to help characterize the patient.

To monitor non-ambulatory, hospitalized patients, conventional vital sign monitors include ECG monitoring systems that characterize a patient's cardiac response in a similar way to holter or event monitors. Such monitors typically measure multi-lead ECG waveforms that are processed by embedded software within the monitor to generate ECG waveforms and determine HR and a wide range of other cardiac properties.

During a conventional EP procedure, software systems can collect physiological information from the patient (e.g. vital signs and ECG waveforms), which is then used to help guide the procedure. These data are also stored in the patient's EMR, where they can be used for future analysis by cardiologists and other clinicians. ECG systems used during EP procedures typically measure 12 leads of ECG waveforms, which a cardiologist then interprets to elucidate, diagnose, and ultimately treat the electrical activities of the patient's heart. Additionally, during EP, an invasive catheter records spontaneous activity of the heart, as well as cardiac responses to programmed electrical stimulation (PES). In addition to these diagnostic and prognostic procedures, an EP cardiologist uses therapeutic methods, such as radio frequency ablation of pre-determined portions of the heart, to adjust the patient's cardiac rhythm to a relatively stable state. ECG-monitoring devices used in the EP procedure measure the response of the injured or cardiomyopathic myocardium to PES on specific pharmacological regimens in order to assess the likelihood that the regimen will successfully prevent potentially fatal sustained ventricular tachycardia (VT) or ventricular fibrillation (VF) in the future. Sometimes a series of drug trials are conducted before and/or after an EP procedure to enable the cardiologist to select a regimen for long-term treatment that best prevents or slows the development of VT or VF following PES. Other therapeutic modalities employed in this field include antiarrhythmic drug therapy and IDs. Such studies may also be conducted in the presence of a newly deployed ID.

Modern IDs also include electronic circuitry for recording and storing cardiac parameters, such as arrhythmia information, HR, HR variability, and data describing the performance of the implanted device. Typically the ID stores this information within a computer memory that can be interrogated over a short-range wireless interface by a specialized device within a cardiologist's office called a 'programmer'. Both the programmer and ID are typically designed and manufactured by the same company. Medtronic, the world's largest manufacturer of IDs, also makes a software system called 'Paceart' that receives, stores, and displays scheduling information and data generated by all major manufacturers of IDs, e.g. Medtronic, Boston Scientific, St. Jude, and Biotronix. The programmer typically includes a computer, display, ECG-measuring system, thermal printer, and a wand that is placed over the implanted device to read information over a short-range, wireless interface. Once read, the computer stores information generated by the ID, and at a later time can import this information into the patient's EMR, where it can be used to further diagnose the patient.

Many conventional EMRs are large software systems hosted on computer servers within a hospital or medical clinic. Some EMRs reside in 'the cloud', meaning they are hosted on remote, Internet-connected computer servers (located, e.g., in a third-party data center), which then render a graphical user interface (GUI) to hospital clinicians with a conventional web browser. In most instances, hospital administrators and clinicians use either the EMR or a secondary software system to performancillary functions related to the EP procedure, such as scheduling, billing, and patient follow-up.

SUMMARY OF THE INVENTION

As described above, a collection of hardware and software systems can collect and store a patient's cardiovascular information before a cardiologist conducts a procedure for EP or an ID, during the actual procedure, and after the patient leaves the hospital or medical clinic. In theory, data during each of these phases flows into the patient's EMR. But, in reality, even state-of-the-art EMRs are only able to collect and store limited amounts of data from these systems, especially when multiple, disparate systems are used to monitor the patient. And typically the data are not organized or formatted in a way that allows processing large data sets measured before, during, and after an EP procedure. Analysis of such data, if it were possible, would facilitate sophisticated inter-site clinical studies with a large number of patients. This, in turn, could yield analysis and development of new therapies, devices, and treatment protocols for cardiovascular patients.

With this in mind, the present invention provides an improved, Internet-based system that seamlessly collects cardiovascular data from a patient before, during, and after a procedure for EP or an ID. For example, during an EP procedure, the system collects information describing the patient's response to PES and the ablation process, ECG waveforms and their various features, HR and other vital signs, HR variability, cardiac arrhythmias, patient demographics, and patient outcomes. Once these data are collected, the system stores them on an Internet-accessible computer system that can deploy a collection of user-selected and custom-developed algorithms. Before and after the procedure, the system also integrates with body-worn and/or programmers that interrogate implanted devices to collect similar data while the patient is either ambulatory, or in a clinic associated with the hospital. A data-collection/storage module, featuring database interface, stores physiological and procedural information measured from the patient. Interfacing with the database is a data-analytics module that features a collection of algorithm-based tools run by computer code (e.g. software) that can collectively analyze information measured during each of these phases from large sets of patients. The data-analytics module also includes an Internet-based GUI that renders these data and exports them for future analysis. Patients providing data for this system may be associated with a single site, or multiple, disparate sites. Analysis of the data, for example, can yield reports that characterize the efficacy of a given procedure, or help a clinician improve a cardiac EP procedure for a given patient. In this way, the present invention can facilitate 'virtual clinical trials' wherein sophisticated multi-center studies are quickly and efficiently performed, all without the significant financial and time investments normally required for conventional clinical trials.

In general, the data-analytics module can perform a spectrum of calculations, ranging from simple statistical analyses (e.g. the number of EP procedures performed by a clinic, or the amount of financial reimbursement received by the clinic) to complex analysis of physiological data (e.g. Boolean searches, subsequent analyses, and image processing). Such analysis can be performed with pre-determined reporting tools, or by exporting customized data fields that can be analyzed off-line using custom algorithms.

Software associated with algorithms deployed by the data-analytics module, for example, can analyze numerical vital signs or waveforms, parameters associated with the EP procedure, parameters associated with the ID, two and three-dimensional images related to the patient's cardiovascular behavior, demographic information, and billing and financial information. These data can be analyzed, for example, to estimate or predict the condition of the patient, determine the efficacy of the EP procedure as applied to the patient, evaluate an ID and its associated components (e.g. leads), evaluate financial aspects of hospital or clinic, and evaluate demographics associated with cardiovascular issues. Alternatively, these algorithms can be used for purposes more suited to scientific research, e.g. for collectively analyzing components of ECG waveforms corresponding to large groups of patients receiving a particular EP procedure to estimate the overall efficacy of the procedure. Components of the ECG waveforms analyzed in this manner include: i) a QRS complex; ii) a P-wave; iii) a T-wave; iv) a U-wave; v) a PR interval; vi) a QRS interval; vii) a QT interval; viii) a PR segment; and ix) an ST segment. The temporal or amplitude-related features of these components may vary over time, and thus the algorithmic-based tools within the system, or software associated with the algorithm-based tools, can analyze the time-dependent evolution of each of these components. In particular, algorithmic-based tools that perform numerical fitting, mathematical modeling, or pattern recognition may be deployed to determine the components and their temporal and amplitude characteristics for any given heartbeat recorded by the system.

In one embodiment, for example, ECG waveforms may be numerically 'fit' with complex mathematical functions, such as multi-order polynomial functions or pre-determined, exemplary ECG waveforms. These functions may then be analyzed to determine the specific components, or changes in these components, within the ECG waveform. In related embodiments, ECG waveforms may be analyzed with more complex mathematical models that attempt to associate features of the waveforms with specific bioelectric events associated with the patient.

Each of the above-mentioned components corresponds to a different feature of the patient's cardiac system, and thus analysis of them according to the invention may determine or predict different cardiac conditions. These conditions and their associated components include: blockage of arteries feeding the heart (each related to the PR interval); aberrant ventricular activity or cardiac rhythms with a ventricular focus (each related to the QRS interval); prolonged time to cardiac repolarization and the onset of ventricular dysrhythmias (each related to the QT interval); P-mitrale and P-pulmonale (each related to the P-wave); hyperkalemia, myorcardial injury, myocardial ischemia, myocardial infarction, pericarditis, ventricular enlargement, bundle branch block, and subarachnoid hemorrhage (each related to the T-wave); and bradycardia, hypokalemia, cardiomyopathy, and enlargement of the left ventricle (each related to the U-wave). These are only a small subset of the cardiac conditions that may be determined or estimated through analysis of the ECG waveform according to the invention.

Algorithmic-based tools, or software associated with these tools, can also analyze relatively long traces of ECG waveforms (spanning over seconds or minutes) measured before, during, and after the EP procedure to characterize: i) a given patient; ii) the efficacy of the EP procedure applied to that patient; iii) a given patient's need for an EP procedure; or iv) the overall efficacy of the EP procedure as applied to a group of patients. For example, analysis of relatively long traces of ECG waveforms in this manner may indicate cardiac conditions such as cardiac bradyarrhythmias, blockage of an artery feeding the heart, acute coronary syndrome, advanced age (fibrosis), inflammation (caused by, e.g., Lyme disease or Chaga's disease), congenital heart disease, ischaemia, genetic cardiac disorders, supraventricular tachycardia such as sinus tachycardia, atrial tachycardia, atrial flutter, atrial fibrillation, junctional tachycardia, AV nodal reentry tachycardia and AV reentrant tachycardia, reentrant tachycardia, Wolff-Parkinson-White (WPW) Syndrome, Lown-Ganong-Levine (LGL) Syndrome, and ventricular tachycardia. Likewise, analysis of these cardiac conditions by analyzing the ECG waveforms may indicate the efficacy of the EP procedure.

In one aspect, the invention features a system for evaluating a patient that includes: i) a first ECG-measuring system that senses ECG information from the patient; ii) a data-acquisition system interfaced to a vital sign-monitoring system that senses vital sign information from the patient during a cardiac EP procedure; and iii) a software system interfaced to both the ECG-measuring system and the data-acquisition system. The software system typically connects to the Internet, meaning that it can be hosted on a remote server that resides outside of the hospital. It typically includes a GUI (e.g. a web page), rendered by a web browser, which a user may view with a computer or mobile device, such as a cellular telephone or tablet computer. The software system features: i) a first software interface that receives ECG information sensed by the ECG-measuring system; ii) a second software interface that receives vital sign information from the data-acquisition system and sensed by the vital-sign monitoring system; iii) a database that stores ECG information sensed from the patient before and after the EP procedure, and vital sign information sensed during the EP procedure by the vital sign monitor; and iv) an algorithm that evaluates the EP procedure by collectively analyzing ECG information sensed from the patient before, during and/or after the EP procedure.

In preferred embodiments, the algorithm compares a first set of parameters extracted from ECG information sensed from the patient before the EP procedure to a second set of parameters extracted from ECG information sensed from the patient after the EP procedure. The first and second sets of data are collected from either an individual patient or large groups of patients. Using this information, the algorithm can estimate the efficacy of a given EP procedure, and convey this in the form of an Internet-accessible report to a clinician. For example, operating in this capacity, the algorithm can analyze HR information, arrhythmia information, or morphology of the ECG waveform, e.g. an ECG QRS complex or QT interval. It then uses this information to evaluate a specific procedure.

In preferred embodiments, the database is configured to store information from a collection of patients. Here, the system may deploy algorithms that rely on advanced computational techniques, such as a numerical fitting algorithm, mathematical modeling, image analysis, and/or pattern recognition. The algorithm may calculate, for example, statistics describing the efficacy of an EP procedure performed on each patient within the group of patients, and following the calculation generate a report describing the statistics. In general, the system can perform a wide range of algorithms and, in response generate multiple types of clinical reports to improve the efficacy of the EP procedure.

In other embodiments, the ECG-measuring system is a body-worn system that can include, e.g., an analog ECG front end, a processing system, and an interface to the Internet. The interface can be either wired or wireless, and may include a conventional mobile device, such as a cellular telephone or tablet computer. The mobile device used to transmit information to the system may be the same one used to view reports and GUIs generated by the system. The system can include both first and second ECG-measuring systems than can be the same system, or different systems. Typically the first ECG-measuring system senses ECG information from the patient before the EP procedure, and the second ECG-measuring system senses ECG information from the patient after the EP procedure. Both the first and second ECG-measuring systems can be body-worn systems that are worn on the outside of the patient's body. Alternatively, one or both of the ECG-measuring systems can be an implanted system, e.g. one that comprises a pacemaker or other ID.

In another aspect, the invention provides a system for evaluating a degree of blockage of a patient's heart. The system features a database that stores a set of data fields collected from a plurality of patients, with each data field in the set corresponding to an individual patient, and including an ECG waveform and a parameter indicating a degree of blockage of an artery feeding the individual patient's heart. An ECG-analysis algorithm included in the system processes the ECG waveform in each data field to extract a set of parameters, and correlates the set of parameters to the parameter indicating the degree of blockage. An averaging algorithm included in the system processes multiple data fields, with each data field corresponding to an individual patient, to determine an average correlation factor mapping the set of parameters to the parameter indicating the degree of blockage. The system also includes an ECG-measuring system (e.g. a body-worn ECG monitor) configured to measure an ECG waveform from a given patient and then transmit a numerical representation of the ECG waveform to the database (e.g. through a wired or wireless connection). Finally, a correlation algorithm evaluates the degree of blockage by extracting a new set of parameters from the ECG waveform measured by the ECG-measuring system, and then comparing the new set of parameters to the average correlation factor to estimate a new parameter indicating the degree of blockage of an artery feeding the given patient's heart.

In specific embodiments, the average correlation factor correlates an average value of the PR interval to the degree of blockage of an artery feeding the heart. For example, when the PR interval exceeds a pre-determined value (e.g. about 200 ms), or alternatively when the PR interval has a temporal variation that exceeds a pre-determined value (e.g. about 25%), the system indicates that a blockage exists for the given patient.

In another aspect, the invention provides a system for evaluating a presence of p-mitrale and p-pulmonale in a patient's heart. Here, the system includes a database that stores a set of data fields collected from a plurality of patients, with each data field in the set corresponding to an individual patient and including a value of an amplitude or width of a P wave extracted from an ECG waveform, and a parameter indicating the presence of p-mitrale and p-pulmonale in the individual patient's heart. An averaging algorithm processes multiple data fields in the database, with each data field corresponding to an individual patient, to determine an average correlation factor mapping the value of the amplitude or width of the P wave to the parameter indicating the presence of p-mitrale and p-pulmonale in a patient's heart. As in the previous aspect, an ECG-measuring system (e.g. a body-worn system) measures an ECG waveform from a given patient and then transmits a numerical representation of the ECG waveform to the database. Finally, a correlation algorithm evaluates the presence of p-mitrale and p-pulmonale in the given patient's heart by extracting a new amplitude or width of the P wave from the ECG waveform measured by the ECG-measuring system, and then comparing the new amplitude of the P wave to the average correlation factor to estimate a new parameter indicating the presence of p-mitrale and p-pulmonale in the given patient's heart. For example, the system may indicate that the patient has a cardiac condition such as p-mitrale or p-pulmonale when the width of the P wave is greater than about 50 ms, or the amplitude of the P wave is greater than about 10% of the amplitude of a QRS complex measured from the same ECG waveform.

In another aspect, the invention provides a system for evaluating a presence of at least one of myocardial ischemia, myocardial infarction, pericarditis, ventricular enlargement, bundle branch block, and subarachnoid hemorrhage. The system uses similar components to those described above, only it features a database comprising a set of data fields collected from a plurality of patients, with each data field in the set corresponding to an individual patient and including a T wave extracted from an ECG waveform and a parameter indicating at least one of the above-described maladies. For example, an inverted T wave may indicate such a condition.

In yet another aspect, the invention provides a system for evaluating an efficacy of an electrophysiology procedure. The system includes a software interface configured to receive ablation locations indicating where a patient's heart has been ablated during a cardiac electrophysiology (EP) procedure, and store numerical representations of the ablation locations in a database. An ECG-measuring system then measures a time-dependent ECG waveform from the patient after the EP procedure, and transmits the numerical representation of the ECG waveform to the same database. A first algorithm processes the numerical representations of the time-dependent ECG waveform to determine a heart rate and heart rate variability. And a second algorithm compares a first set of numerical values indicating the ablation locations to the heart rate and heart rate variability to determine a parameter estimating the efficacy of the EP procedure.

The invention has many advantages. In general, a cloud-based system that connects to the Internet from a remote server typically offers more flexibility than a system that is deployed in the same facility (e.g. a hospital or medical clinic) used to perform the EP procedure. With such a system, information from multiple, diverse patient groups can be collectively analyzed to perform sophisticated research relating to EP and other cardiovascular procedures. This facilitates 'virtual clinical trials', as described above, which can be conducted efficiently and inexpensively. The same system that performs the research can also generate reports and other materials using data from large groups of patients that can easily be dispersed to clinicians, thereby giving them the tools to improve their clinical practice. Moreover, Internet-based systems, i.e. systems that leverage 'the cloud', are inherently easier to maintain (e.g. deploy, update) compared to hosted client-server systems deployed at a collection of facilities, as new software builds and enhancements can be made on a single server, and then instantaneously deployed to multiple Internet-connected sites.

These and other advantages will be apparent from the following detailed description, and from the claims.

BRIEF DESCRIPTION OF THE DRAWINGS

FIG. 2-1 shows exemplary database tables that describe patient demographics and physiological information;

FIG. 2-2 depicts schematically the mapping of ECG waveforms collected from a patient to a corresponding data table;

FIG. 11 shows a screenshot from a website associated with the data-analytics module that collects a variety of data fields and exports them to a data table for follow-on analysis;

DETAILED DESCRIPTION OF THE INVENTION

The invention provides an Internet-based system that features data-collection/storage and data-analytics modules that, collectively, allow effective analysis of large data sets to improve cardiovascular medicine. During use, the data-collection/storage module collects cardiovascular and other patient and device-related data before, during, and after an EP or ID procedure, and then stores data from large groups of patients in a relational database. It interfaces with a data-analytics module that accesses and processes data from the database with a collection of algorithms to yield distilled information, which a website then renders for clinicians and other users. In general, the data collection/storage module integrates with the data-analytics module to process data and further distill it to provide useful information to a user. These systems operate in concert to perform a range of numerical analyses, from simple statistical analyses to complex, multi-parameter numerical studies that investigate patient physiology and efficacies of specific procedures.

In embodiments, the system collects information describing ECG waveforms and various components found therein, HR, HR variability, cardiac arrhythmias, performance of IDs, patient demographics, and patient outcomes, and stores them on an Internet-accessible computer system that can deploy a collection of algorithms. Using a simple GUI available through the Internet, clinicians can deploy the algorithms to improve their practice and better manage their patients.

Figure 1:
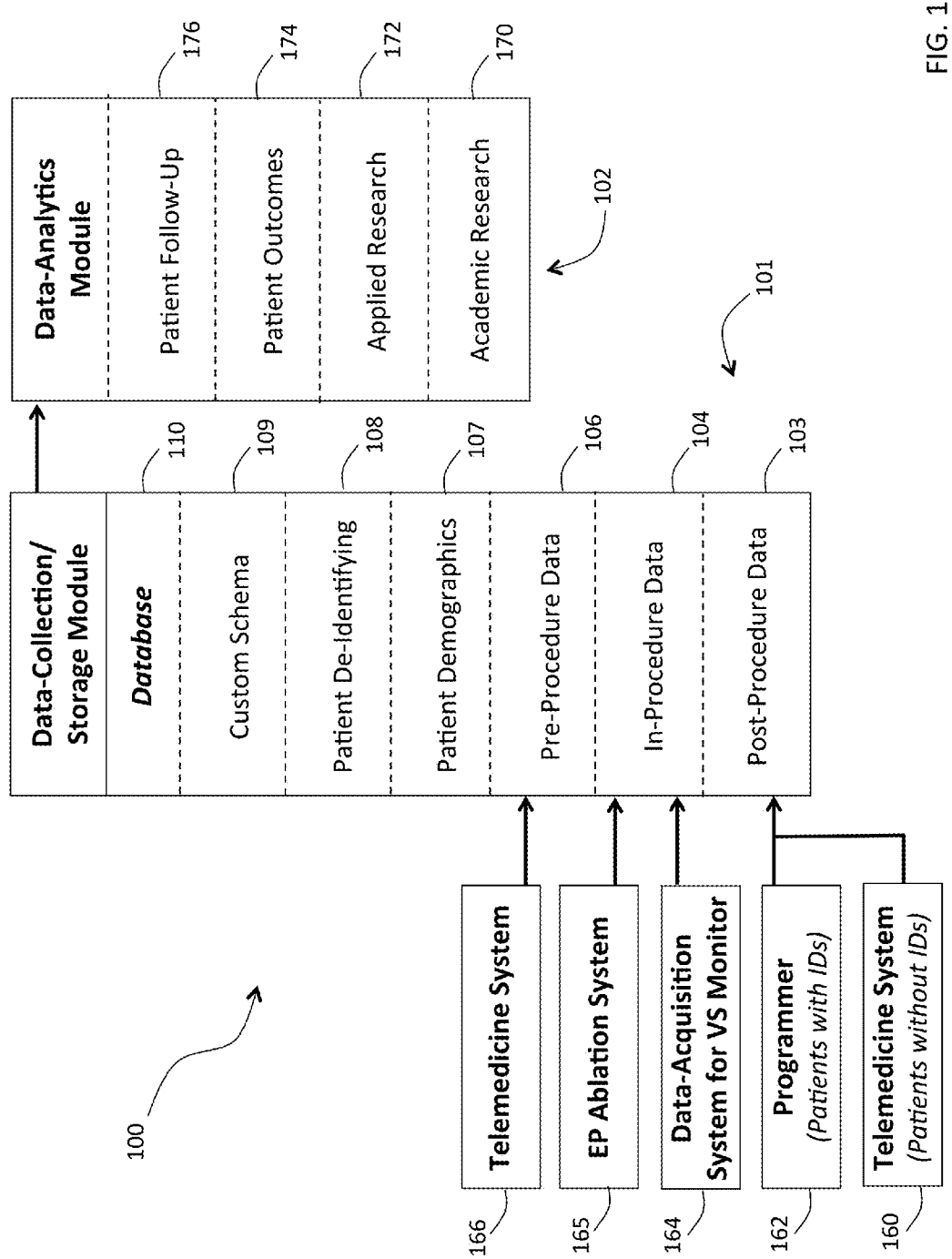
FIG. 1 shows a schematic drawing of a system according to the invention that includes a data-collection/storage module that collects cardiovascular information from a patient and a collection of hardware devices and stores the information in a database, and a data-analytics module that collectively analyzes the information to characterize the patient.

FIG. 1 shows a system 100 according to the invention. The system 100 is an Internet-based software system that features a collection of computer code, and typically operates on a remote computer system (e.g. one residing in a data center). The system 100 features a data-collection/storage module 101, and a data-analytics module 102. The data-collection/storage module 101 features a database 110 that includes an array of data fields and tables that store patient demographics 107, pre-procedure data 106, in-procedure data 104, and post-procedure data 103. These data are typically collected by multiple physiological monitoring systems. For example, a patient can wear a telemedicine system 166, such as a body-worn ECG monitoring system, to collect the pre-procedure data 106 outside of the hospital. Such a system, which is described in more detail with reference to FIG. 15, typically collects real-time ECG waveforms, arrhythmia data, HR data, and other information from the patient during a short period (e.g. a few days to several weeks) before the actual EP procedure. These data can be ported into the pre-procedure data field 106 through a wired or, more preferably, a wireless interface, such as a cellular interface. In embodiments, the telemedicine system may be programmed to automatically send information to the data-collection/storage module 101, i.e. it is programmed to automatically send information to a specific IP address associated with this system. Alternatively, a third-party vendor may manufacture the telemedicine system 166, and this in turn integrates with the data-collection/storage module through a software interface, such as a web service interface. Here, the web service interface typically sends an XML file, which is then parsed with a software system residing with the data-collection/storage module. In other embodiments, the data-collection/storage module 101 collects pre-procedure physiological data from a collection of telemedicine systems 166, each manufactured by one or more outside vendors. In each case, a schema associated with the pre-procedure data fields 106 is used to describe the specific data elements that flow into the database 110.

The data-collection/storage module 101 collects data before, during, and after the actual EP procedure by integrating with a telemedicine system 166, EP ablation system 165, data-acquisition system for a vital sign (VS) monitor 164, a programmer 162 that interrogates patients with IDs, and a second telemedicine system 160 for patients without IDs. Each of these systems provide numeric and waveform data for the data-collection/storage module. More specifically, the telemedicine systems 160, 166 are typically body-worn ECG holter or event monitors, like those described above, that generate ECG waveforms, HR values, and other information describing the patient's cardiac rhythm (e.g. HR variability, arrhythmia information). The EP ablation systems generate data describing the EP process, e.g. ablation energies and durations, mapping of where the ablations took place, catheter location, and time-dependent waveforms generated by catheter-based electrodes that come in direct contact with the patient's heart during an EP procedure. The data-acquisition system 164, for example, can include both hardware and software components that extract numerical and waveform information from a VS monitor, e.g. a serial or parallel data cable and a software system that receives the data (typically in the form of packets), and then parses them appropriately. Alternatively, the data-acquisition system 164 can be a software interface to a middleware system (e.g. one associated with an EMR) that collects data from the VS monitor. In both cases, the data-acquisition system 164 extracts time-dependent waveforms and numerical vital signs such as HR, blood pressure, respiratory rate, blood oxygen, and temperature from the VS monitor used during the EP procedure. In a preferred embodiment, the data-acquisition system 164 extracts data in a quasi-continuous manner during the EP procedure, e.g. a new, updated numerical value is extracted every second or so.

The programmer 162 is typically a computer-based system that resides in a cardiologist's office and includes a short-range wireless component that, when waved over a patient's ID, receives data and then stores it in memory associated with the computer-based system. For example, the short-range wireless component may rely on inductive magnetic coupling to remove physiological data associated with the patient, along with data associated with the performance of the ID, e.g. the number and time/date of defibrillation shocks, and/or battery information. Programmers also typically include ECG systems designed to measure conventional ECG waveforms and associated information, such as HR. Once these and other data are stored on the computer-based system, the programmer 162 transfers it over to the post-procedure data field 103 for future analysis. In embodiments, for example, the programmer 162 may include manufacturer-specific software, such as Medtronic's Paceart System, to facilitate data extraction and transfer. The Paceart System organizes and archives data for cardiac devices across manufacturers and serves as a central repository for a patient's arrhythmia and other information. The system serves as a gateway through which data flows from the computer-based system into a clinic's electronic health record EMR.

A telemedicine system 160 supplies data for the post-procedure data field 103 for patients that lack an ID. Such a telemedicine system 160 is comparable or, more preferably, identical to the telemedicine system 166 used to supply data for the pre-procedure data field 106. It is typically a body-worn system, used to characterize a remote, ambulatory patient, that includes an ECG-monitoring system and computing module that measures, digitizes, and processes analog ECG waveforms to determine parameters such as HR, arrhythmia information, and motion-related information from the patient. The telemedicine system 166 may include a wireless system that sends data from the ambulatory patient to the post-procedure data field 103. Typically the telemedicine system 160 is worn for a period ranging from 1-2 days to several weeks. In other embodiments, the patient uses the telemedicine system 160 on a semi-permanent basis to collect data for a short period of time each day. For example, the telemedicine system 160 may be used by the patient's bedside to collect data each night when the patient is sleeping.

Once extracted, data measured from each of these systems 160, 162, 164, 165, 166 are stored in the appropriate data fields 103, 104, 106 associated with the database 110, and then used for follow-on analysis as described in more detail below. Additionally, the database 110 includes data fields that store parameters related to patient demographics 107, e.g. a patient's name, address, date of birth, age, height, weight, ethnicity, allergies, medications, and social security number.

The data-analytics module 102 features a collection of algorithm-based tools that interface with the data-collection/storage module 101 to process data stored in the pre-procedure 106, in-procedure 104, and post-procedure 103 data fields to generate usable information for the clinician. In preferred embodiments, the algorithm-based tools provide clinicians with a single, integrated system that allows them to analyze data collected from a large number of patients associated with different medical centers, and in doing so research new treatment strategies that may be effective with new patients. For example, the algorithm-based tools may include modules that facilitate patient follow-up 176, help determine patient outcomes 174, and perform applied 172 and academic 170 research studies on large groups of patients to help determine, e.g., the efficacy of certain treatment methodologies. In embodiments, results from the applied 172 and academic 170 research studies could be made available to clinicians through reports generated by the system 100.

Figure 2:
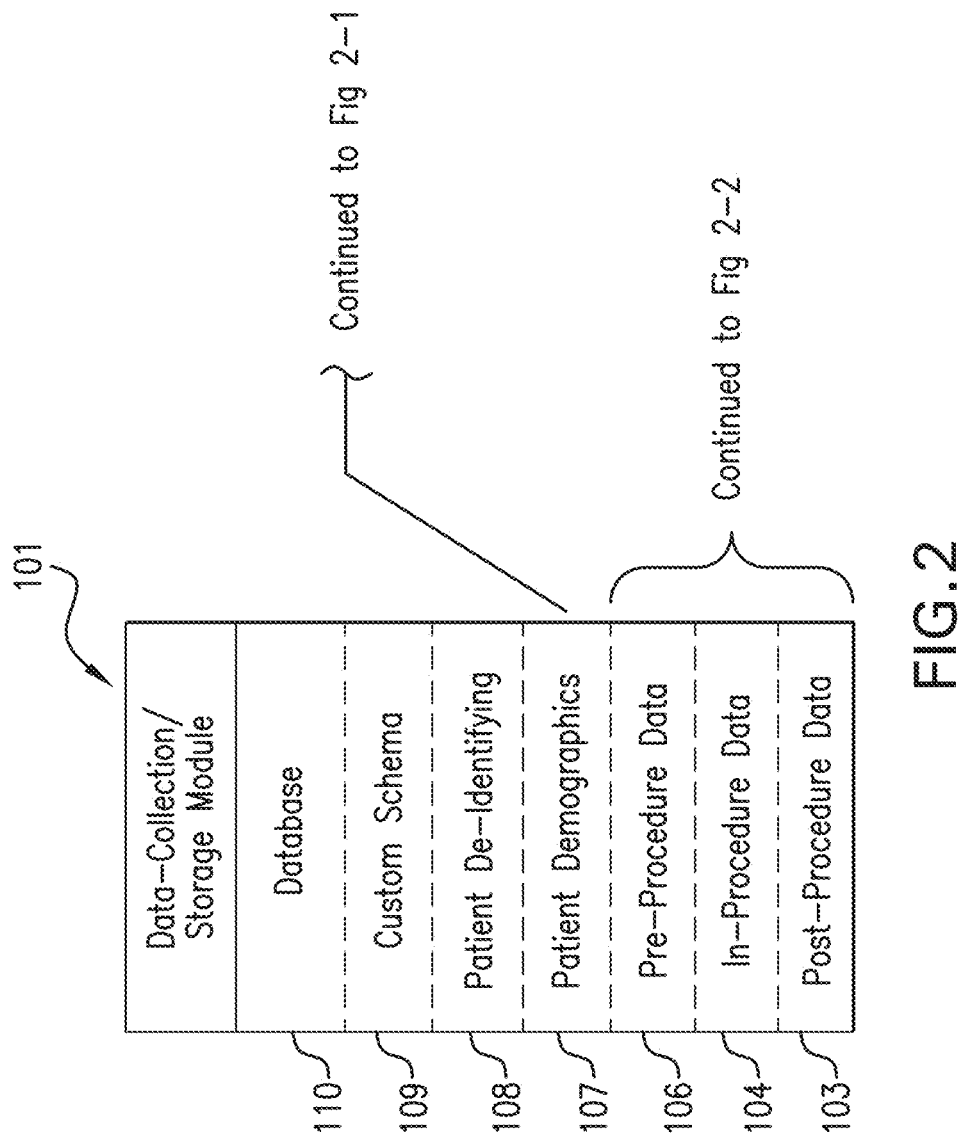
FIG. 2 shows a schematic drawing of the data-collection/storage module of FIG. 1.
Figure 2:
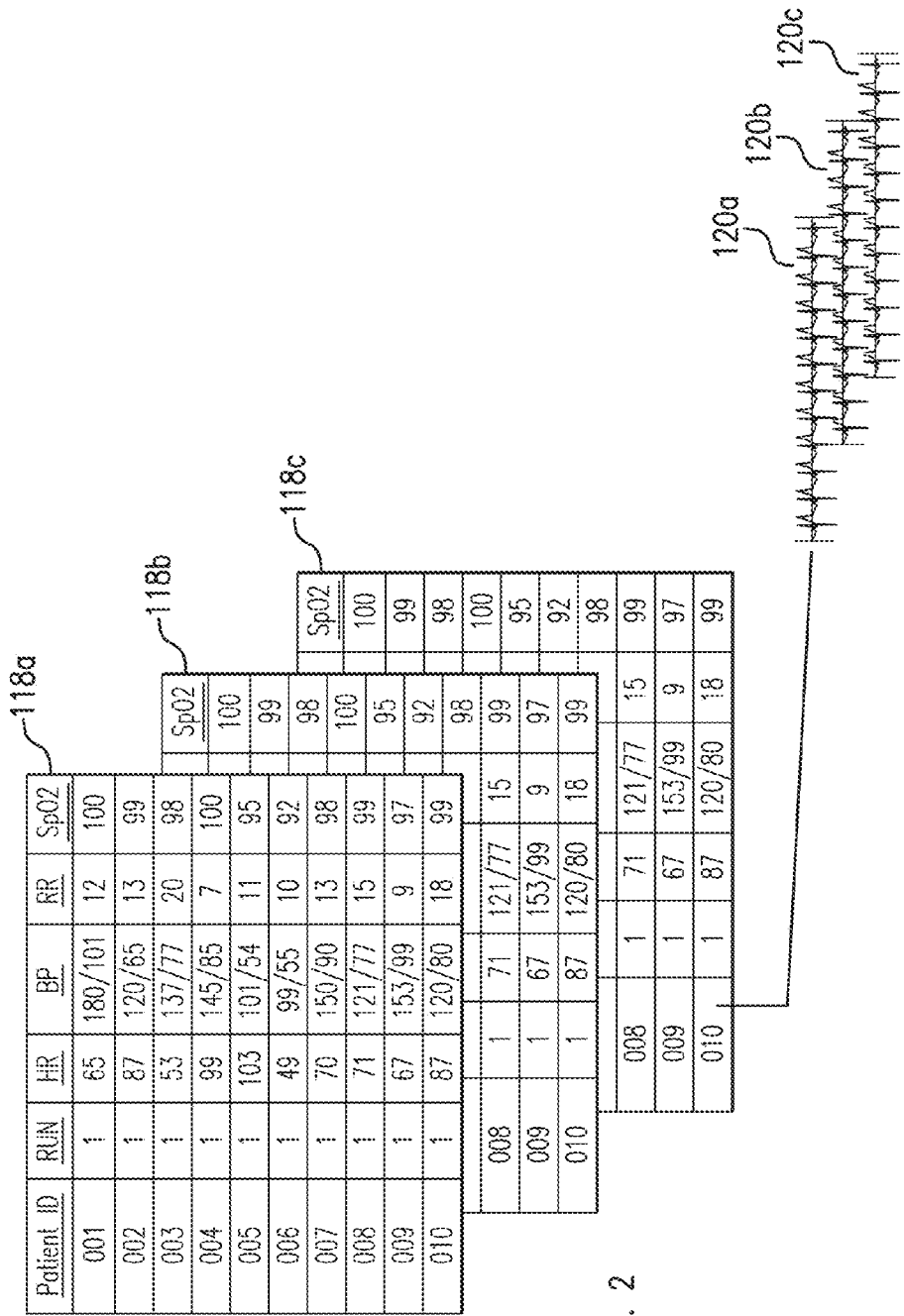

FIG. 2 shows examples of simple data fields within the database 110 associated with the data collection/storage module 101. In embodiments, for example, the database 110 includes a high-level, custom schema 109 that describes relationships between data, patients, clinicians, and hospitals. For example, in embodiments the custom schema 109 groups certain hospitals together which have agreed to share data collected from their respective patients, and also groups clinicians within the hospitals who have privileges to view the data. For research purposes, it will likely be necessary to de-identify these data, e.g. remove personal patient information as per the guidelines set out by the Health Insurance Portability and Accountability Act (HIPAA). De-identification will remove sensitive personal information, but will retain demographics information that is stored in a patient demographics data field 108 featuring simple parameters such as a patient identifier (e.g. number), their gender, date of birth, along with simple biometric parameters such as weight, height, and whether or not the patient has an ID. For example, these data can be organized in standard tables used by commercially available relational databases, such as PostgreSQL, Microsoft SQL Server, MySQL, IBM DB2, and Oracle. Typically the patient identifier within the patient demographics field 108 is a database 'key' that links a particular patient to other data fields. For example, other data fields within the database 110, such as the pre-procedure 106, in-procedure 104, and post-procedure 103 data fields, use this key to link physiological data measured during these particular periods to the patient. These data are found in new tables 118a-c in the database, and typically include physiological data (e.g. numerical values and waveforms) describing parameters such as HR, systolic and diastolic blood pressure (BP), respiratory rate (RR), and blood oxygen (SpO2). Typically these parameters are measured over time (e.g. in a continuous or quasi-continuous manner), and then identified in the tables 118a-c by a 'Run' number that sequentially increases over time. As described above, data for the tables 118a-c is typically measured with a hardware component attached to the patient, such as a telemetry monitor that an ambulatory patient wears outside of the hospital, an ID, or by a VS monitor used to measure the patient during an actual EP procedure.

The database may also associate numerical physiological data for each run with a physiological waveform 120a-c that is analyzed to extract the particular datum. For example, as shown in FIG. 2, the above-mentioned hardware component may measure time-dependent ECG waveforms 120a-c that yield information such as HR and arrhythmia information, and are thus stored in the database. Such waveforms may be processed with the algorithm-based tools described with reference to FIG. 1, such as numerical 'fitting' or beatpicking algorithms, to better diagnose a patient's condition. Although FIG. 2 only shows single-lead ECG waveforms, other physiological waveforms can also be measured, stored, and then processed with the algorithm-based tools described above. These waveforms include multi-lead ECG waveforms, photoplethysmogram (PPG) waveforms that yield SpO2, arterial waveforms that yield BP, and impedance cardiography (ICG) waveforms that yield RR and cardiac parameters such as stroke volume and cardiac output. In embodiments, these waveforms may be associated with another table that includes annotation markers that indicate fiducial points (e.g., the QRS complex in an ECG waveform) associated with certain features in the waveforms. The algorithm-based tools may also process these annotation markers to perform simple patient follow-up, estimate patient outcomes, and do applied and academic research, as described above.

In related embodiments, ECG waveforms may be analyzed with more complex mathematical models that attempt to associate features of the waveforms with specific bioelectric events associated with the patient. For example, mathematical models can be deployed that estimate ECG waveforms by interactively changing the estimated timing associated with depolarization and repolarization of a simulated ventricular surface, as well as the strength of the depolarization and repolarization. The timings and signal strengths associated with these models can then be collectively analyzed to simulate an ECG waveform. The simulated ECG waveform can then be compared to the waveform actually measured from the patient to help characterize their cardiac condition, or the efficacy of the EP procedure that addresses this condition. In general, a wide range of physiological and device-related parameters can be stored in the data tables described above. Examples of some of these data fields corresponding to specific ECP procedures are shown below in Table 1.

In embodiments, commercially available software tools, such as Mortara's E-Scribe Rx and VERITASO ECG algorithms, may be interfaced with the database 110 and used to analyze ECG waveforms measured from the patient. These software tools are designed to analyze complex, multi-lead ECG waveforms to determine complex arrhythmias, VF, VT, etc.

Figure 3:
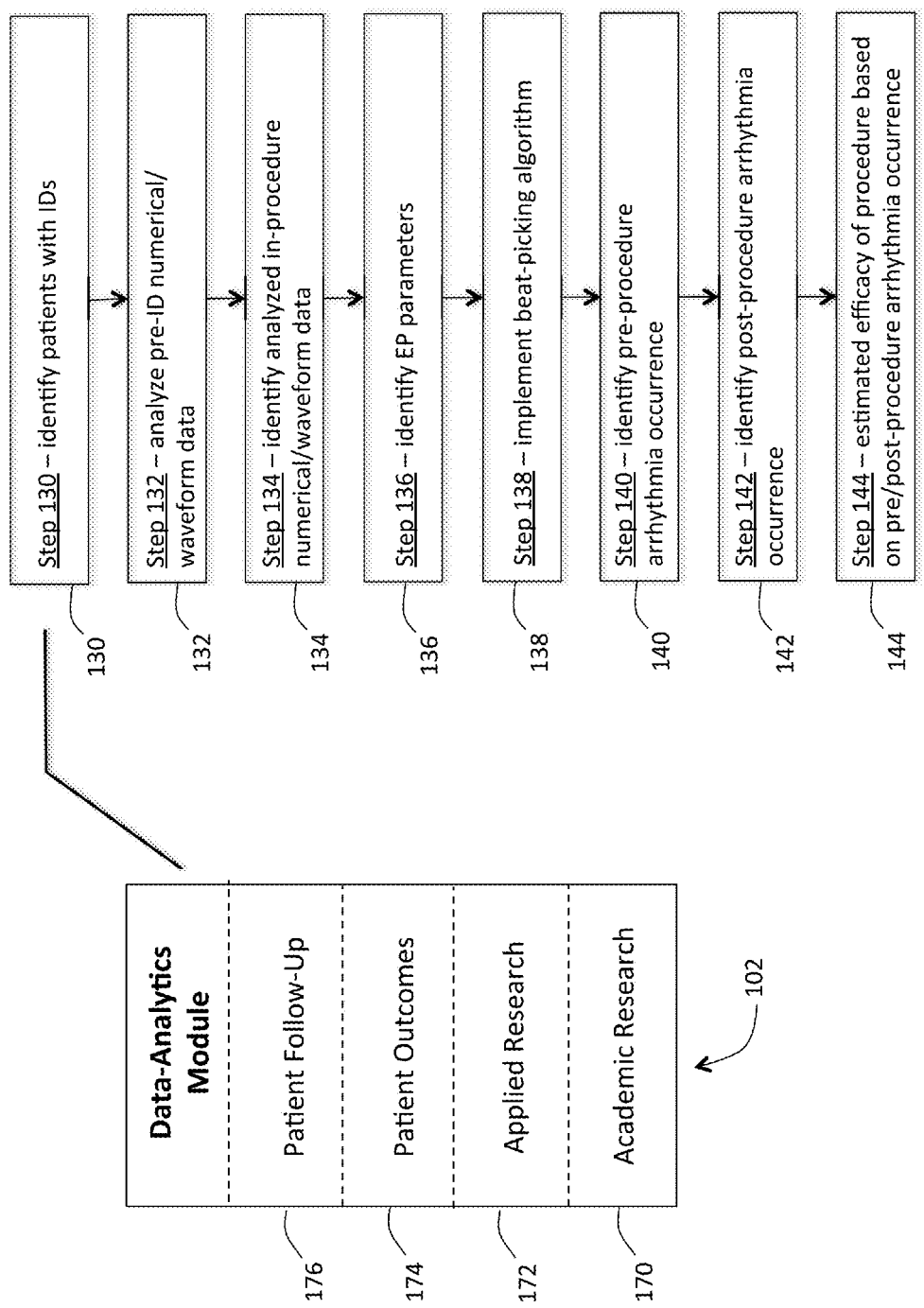
FIG. 3 shows a schematic drawing of the data-analytics module of FIG. 1, featuring an algorithm integrated with the data-collection/storage module of FIG. 2 that analyzes a patient's cardiovascular information.

FIG. 3 shows a simple example of a simple data-analytics module 102 featuring an algorithm-based tool that analyzes patient data from the data-collection/storage module to estimate a patient's outcome. In one specific algorithm associated with the data-analytics module 102, computer code analyzes data fields to first identify patients with IDs (step 130). The code then collects pre-ID (step 132) and in-procedure (step 134) numerical/waveforms data, along with parameters from the patient's EP procedure (step 136), and readies them for analysis. Parameters collected during the patient's EP procedure include parameters associated with the EP catheter used during the EP procedure (such as those described in Table 1), potentials applied by the catheter and their timing, and two and three-dimensional images measured during the procedure. The algorithm then collectively analyzes these data, and implements a beat-picking algorithm (step 138) to further characterize ECG waveforms measured during steps 134 and 136. The beat-picking algorithm can determine parameters such as induced arrhythmia, effective refractory periods, characteristics of specific components within the patient's ECG waveform, e.g. the QRS complex, width of the P-wave, QT period and dispersion, and instantaneous HR.

Using these technologies, the algorithm can perform simple functions like identifying pre-procedure (step 140) and post-procedure (step 142) arrhythmia occurrences, and then comparing these to determine the efficacy of the procedure (step 144). Many other algorithm-based tools, of course, are possible within the scope of this invention.

Other algorithm-based tools are more sophisticated than that described with reference to FIG. 3. In general, these tools can analyze any combination of data that are generated by the telemedicine systems 160, 166, EP ablation system 165, data-acquisition system for the VS monitor 164, and programmer 162 described in reference to FIGS. 1 and 2. Data from the telemedicine systems 160, 166, VS monitors 164, and programmer 162 are described above. Data from the EP ablation system is typically more extensive, and is described below in Table 1.

TABLE 1 data fields associated with specific EP procedures

| Description of Data Field | # of Possible Values | Example Values |
|---|---|---|
| Ablated Locations | 35 | AV Node Modification (Fast pathway), Bundle Branch, Complex fracionated atrial electrograms (CFAE), Crista Terminalis, LA Anteroseptal line, LA CS Line, Left atrium, RIGHT ATRIUM, Accessory Pathway, AV Node, Cavo-tricuspid isthmus, Endocardial, Epicardial, Fast pathway, Intermediate pathway, LEFT CIRCUMFERENTIAL PULMONARY, Segmental antral left lower pulmonary vein, Segmental antral left lower pulmonary vein, MITRAL ISTHMUS, Fast pathway, Left Atrial Linear (Mitral Isthmus), Right Circumferential Pulmonary, Left Atrial Linear (Mitral Isthmus), Endocardial, Right Circumferential Pulmonary, EPICARDIAL, Segmental antral right lower pulmonary vein, Left Atrial Linear (Roof), Segmental antral right upper pulmonary vein, Segmental antral right upper pulmonary vein, SVC, Slow pathway, Segmental antral right lower pulmonary vein. |
| Sub-Locations | 106 | Left Circle, LV Septal Basal, CS middle, Lower crista, LA septal wall, Mitral Valve Annulus, RA lateral wall, Left Antero-Lateral, Non-Coronary Cusp, Upper crista, RVOT Anterior, LA Scar, Atrio-Ventricular, Left Lateral, Right Mahaim, CS proximal, Atrio-Fasicular, Right Mid-Septal, RV Posterior Basal, CS distal, LA appendage, LA anterior wall, Lower Loop, Left Aortic Cusp, LV anterior Fascicle, LA septum, RV Anterior Apical, LV Posterior Mid, LV Posterior Fascicle, LV Posterior Apical, RV Anterior Mid, LLPV, RLPV, RVOT Free Wall, RV Septal Apical, RV Lateral Mid, Mitral Isthmus (with CS), Right Postero-Lateral, RBB, LV Lateral Basal, Left Antero-Septal, RA septal wall, LV Septal Apical, MVA anterior, LV Outlow Tract, Upper Loop, Pulmonary Artery, Right Antero-Lateral, TVA lateral, Right Aortic Cusp, RA Scar, Right Posterior, RA anterior wall, Mitral Isthmus (endocardial only), RV Posterior Apical, CSos, LV Anterior Mid, RV Lateral Basal, Left Mahaim, TVA posterior, RA poseterior wall, Nodo-Fasicular, LV Lateral Mid, RA appendage, Cavo-Tricuspid Isthmus, LA lateral wall, RVOT Posterior, Middle crista, Superior Vena Cava, Left Posterior, LV Anterior Basal, Fossa ovalls, LV Septal Mid, LUPV, Diverticular, Diverticuar, SVC, Non-Coronary Aortic Cusp, TVA anterior, Right Lateral, RVOT Septal, MVA septal, RUPV, LA posterior wall, Right Postero-Septal, MVA posterior, Nodo-Ventricular, MVA lateral, RV Anterior Basal, LV Lateral Apical, Left Postero-Septal, Right Antero-Septal, LVOT, RV Septal Mid, Left Postero-Lateral, RV Septal Basal, LA roof, Left bundle branch, LA poseterior wall, RV Posterior Mid, RA septum, RV Outflow Tract Anterior, RV Lateral Apical, Csos, LV Posterior Basal, Right Circle |
| Access Locations | 29 | Left Subclavian Vein, Right Antecubital Vein, Right Femoral Vein, Right Subclavian Vein, Right Lower Extremeties/Thigh, Left Antecubital Vein, Superficial Right Leg, Superficial Right Hand/Forearm Vein, Deep Right Hand/Forearm Vein, Right Femoral Artery, Superficial Right Arm Vein, Superficial Left Hand/Forearm Vein, Deep Right Arm Vein, Deep Right Arm Vein, Deep Left Hand/Forearm Vein, Left Femoral Vein, Left Lower Extremeties/Thigh, Right Foot, Right Internal Jugular |

TABLE 1-continued data fields associated with specific EP procedures

| Description of Data Field | # of Possible Values | Example Values |
|---|---|---|
| | | Vein, Superficial Left Leg, Deep Right Leg, Left Femoral Artery, Left Internal Jugular Vein, Deep Left Arm Vein, Left Radial Artery, Right Radial Rrtery, Superficial Left Arm Vein, Left Foot, Deep Left Leg |
| Arrhythmia Mechanism | 20 | Idiopathic ventricular tachycardia, Atrial Fibrillation Paroxysmal, AV Nodal Reentry (fast-slow), AV Nodal Reentry (slow-slow), Premature ventricular contractions, Atrial Fibrillation Persistent, Atypical Left Atrial Flutter, Atypical Mitral Isthmus Flutter, Bundle Branch Reentry VT, Inappropriate Sinus Tachycardia, Structural ventricular tachycardia - Dilated Cardi, AV Nodal Reentry (slow-fast), Focal Atrial Tachycardia, Antidromic AV reentrant tachycardia, Reverse Typical Atrial Flutter, Atypical Right Atrial Flutter, Typical Atrial Flutter, Structural ventricular tachycardia - Ischemic Card, Wolff-Parkinson-White syndrome, Orthodromic AV reentrant tachycardia |
| Arrhythmia Mechanism Types | 10 | Typical Atrial Flutter, AV nodal reentry (slow-slow), AV nodal reentry (slow-fast), Antidromic AV reentrant tachycardia (ART), Reverse Typcial Atrial Flutter, Ventricular tachycardia, Orthodromic AV reentrant tachycardia (ORT), Atrial Fibrillation, Atypical Atrial Flutter, AV nodal reentry (fast-slow) |
| Arrhythmia Observations | 9 | Vagal Effect, Arrhythmogenic Veins RUPV, Arrhythmogenic Veins LLPV, Concealed Accessory Pathway, Negative CSM, WPW, Positive CSM, Arrhythmogenic Veins LUPV, Arrhythmogenic Veins RLPV |
| Axis Deviations | 6 | Left, Left Inferior, None, Right Inferior, Right, Left Superior |
| Mapping Systems | 8 | Carto 3D electro-anatomical, Fluoroscopy, Ensite 3D Balloon Array, ESI NavX 3D electro-anatomical |
| Energy Sources | 6 | Cryoablation, Laser, Ultrasound, Other, Radiofrequency |
| Morphology | 8 | |
| Pacing Site | 13 | LVA, LRA, LA, RVOT, RVA, LVB, CSP, CSP, LLA, HRA, CSD, CSM, LVOT |
| lu_abl_result | 51 | Intermediate pathway block - not reinducible, Partially Isolated, ORT Reinducible, Right bundle branch block, AV Node Block, AV Node Modified, Fast pathway block - not reinducible, VT Not-reinducible, Conduction Block, Isolated, AVNRT Reinducible, Mitral Isthmus Block (bidirectional), ORT Not Reinducible, Bidirectional CTI Block, AFL Terminated, PVCs eliminated, LLPV Isolated, Left bundle branch block, VT Slowed, WPW Terminated, FAT terminated, ORT Terminated, Reduction in electrogram amplitude to less than 0.5 mV, RMPV Isolated, AP block, not reinducible, RUPV Isolated, AF Terminated, Complete AV Block, Slow pathway block - not reinducible, AF Converted to AFL, AFL Not Reinducible, AP Block, Reduction in electrogram amplitude to less than 0., VT Terminated, Mitral Isthmus Conduction Delay Only, LUPV Isolated, Single AV nodal echo only, ART Reinducible, AF Termination, AP Block, Not Reinducible, ART Not Reinducible, ART Terminated, WPW Reinducible, Mitral Isthmus Block (unidirectional), CTI conduction delay, Incomplete AV Block, Mitral Isthmus Conduction Delay, AP block (antegrade and retrograde), RLPV Isolated, AP block (antegrade only), Unidirectional CTI Block |
| Structural Observations | 8 | Atrial Septal Defect, Patent Foramen Ovale, Common OS Left, Atrial Scarring, LA Thrombus, Common OS Right, Pericardial Effusion |
| Termination Methods | 11 | Cardioversion, Ablation, Burst, Verapamil, Adenosine, Spontaneous, Metropolol, Pvc, Procainamide, Ibutilide, Pac |
| Access Type | 21 | Direct Cutdown, Percutaneous, Epicardial, Swan-Ganz Line, Tunneled Central Line, Arterial Line, Central Venous Pressure Line, Sheath - Hansen, Sheath - Transseptal, Peripherally Inserted Central Catheter, Pulmonary Artery Catheter, Shunt, Sheath - Steerable, Sheath - Standard short, Sheath - Preformed long, Central Venous Line, Peripheral IV, Implantable Port |

Figure 4:
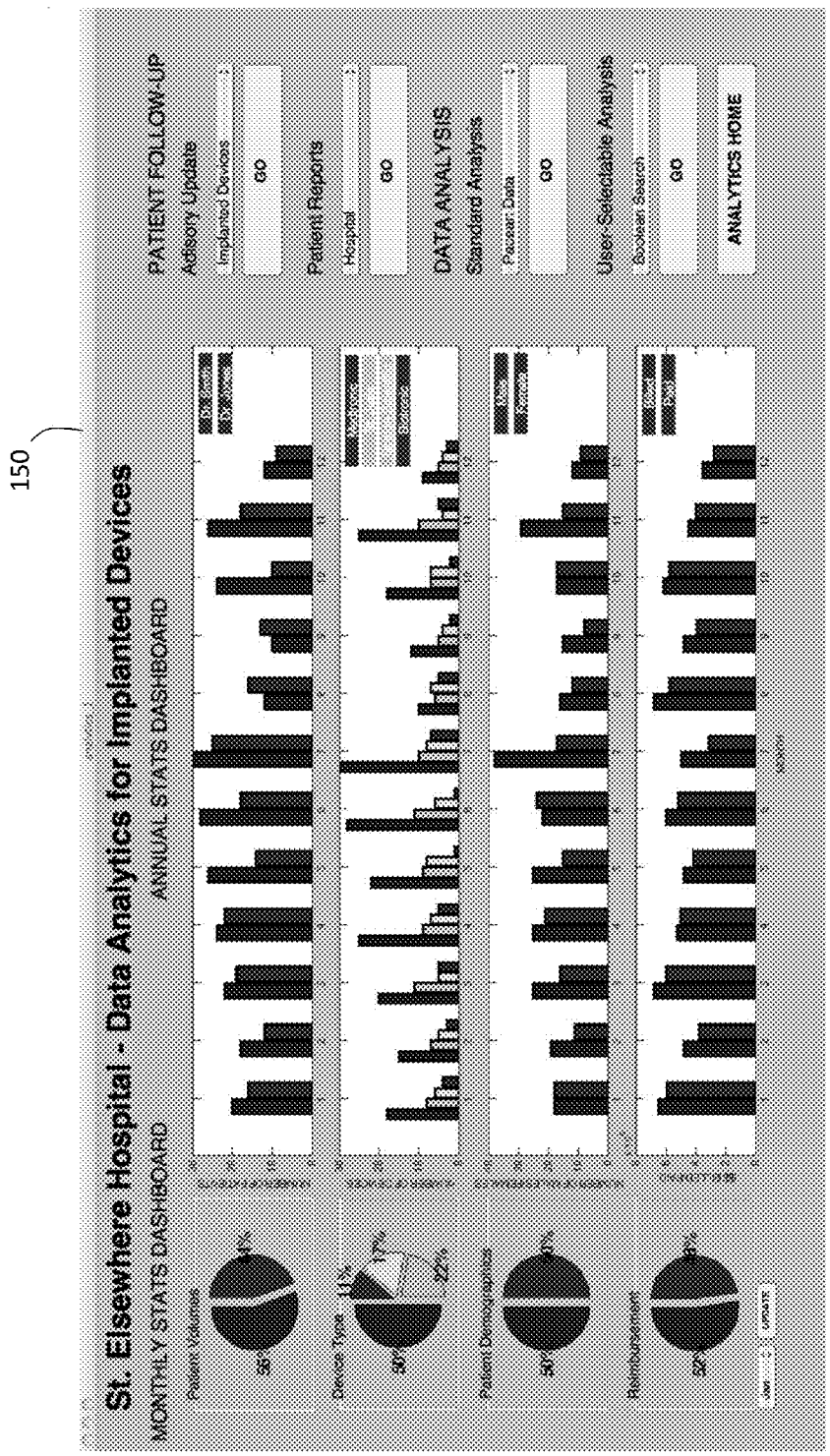
FIG. 4 shows a screenshot from a website associated with the data-analytics module of FIG. 3 that processes and renders numerical data stored in the data-collection/storage module of FIG. 2.

FIG. 4 shows an example screenshot 150 from the data-analytics module. The screenshot 150, for example, could be taken from a GUI of a website. It features three 'areas' of analytics that, informally, vary in terms of their complexity. On the left-hand side of the screenshot 150 are simple pie charts that indicate basis statistics associated with a hospital performing EP procedures. The pie charts render graphics indicating monthly statistics, and show information such as patient volumes, manufacturers of IDs, patient demographics, and financial reimbursements. Similar statistics for previous months are rendered after the user selects the desired month and updates the plots using buttons and pull-down menus at the bottom of the page. The middle area of the page shows monthly bar charts that show similar data for the entire year. Each bar chart and its neighboring pie chart plots similar data. The right-hand area of the screenshot 150 shows a series of persistent buttons that allow clinicians to perform patient follow-up, generate pre-determined reports, and do standard and user-selectable data analyses. These analytical processes are described in more detail below.

Figure 5:
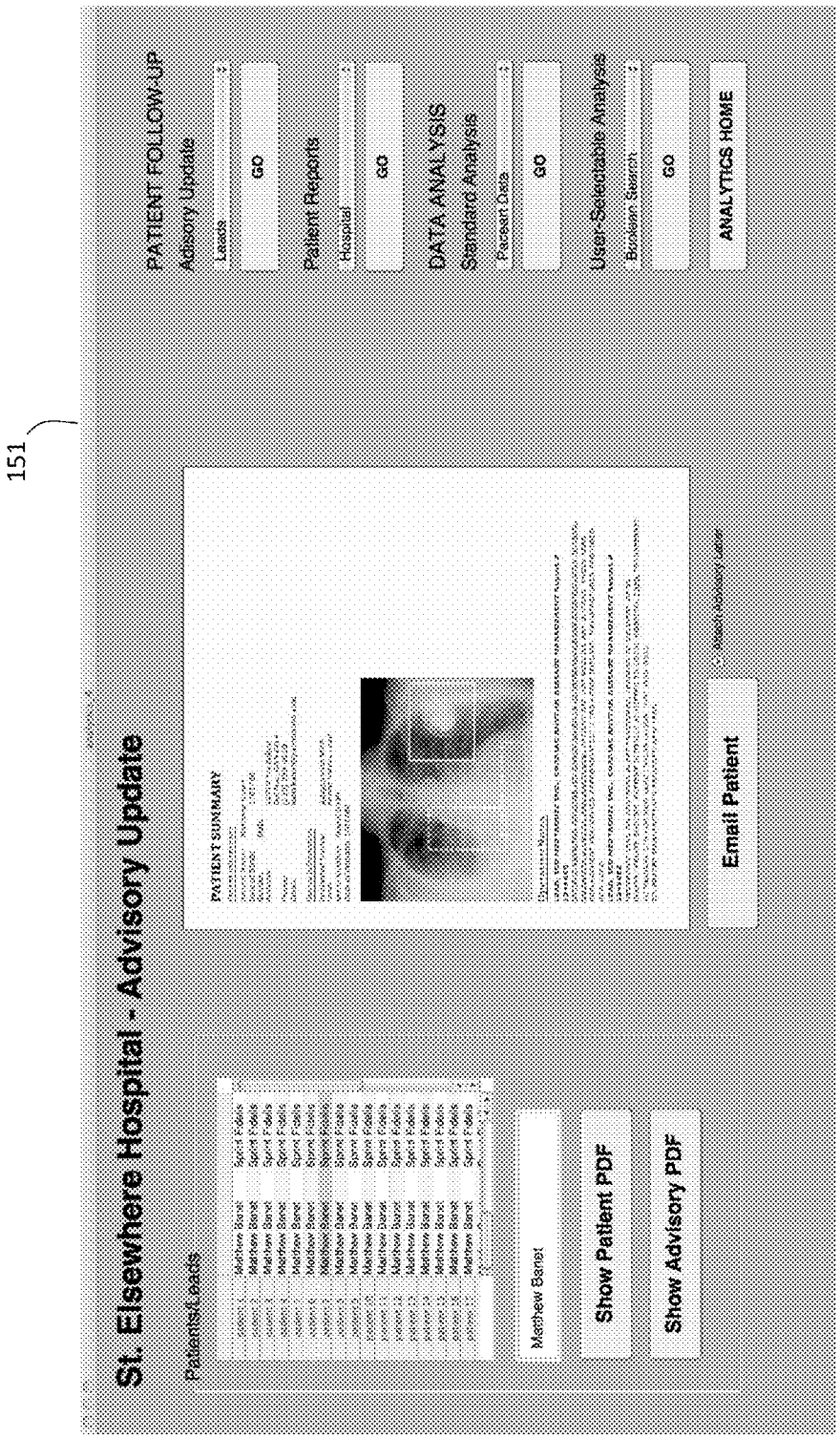
FIG. 5 shows a screenshot from a website of FIG. 4 associated with the data-analytics module that renders a report summarizing a patient's visit to a medical clinic.
Figure 6:
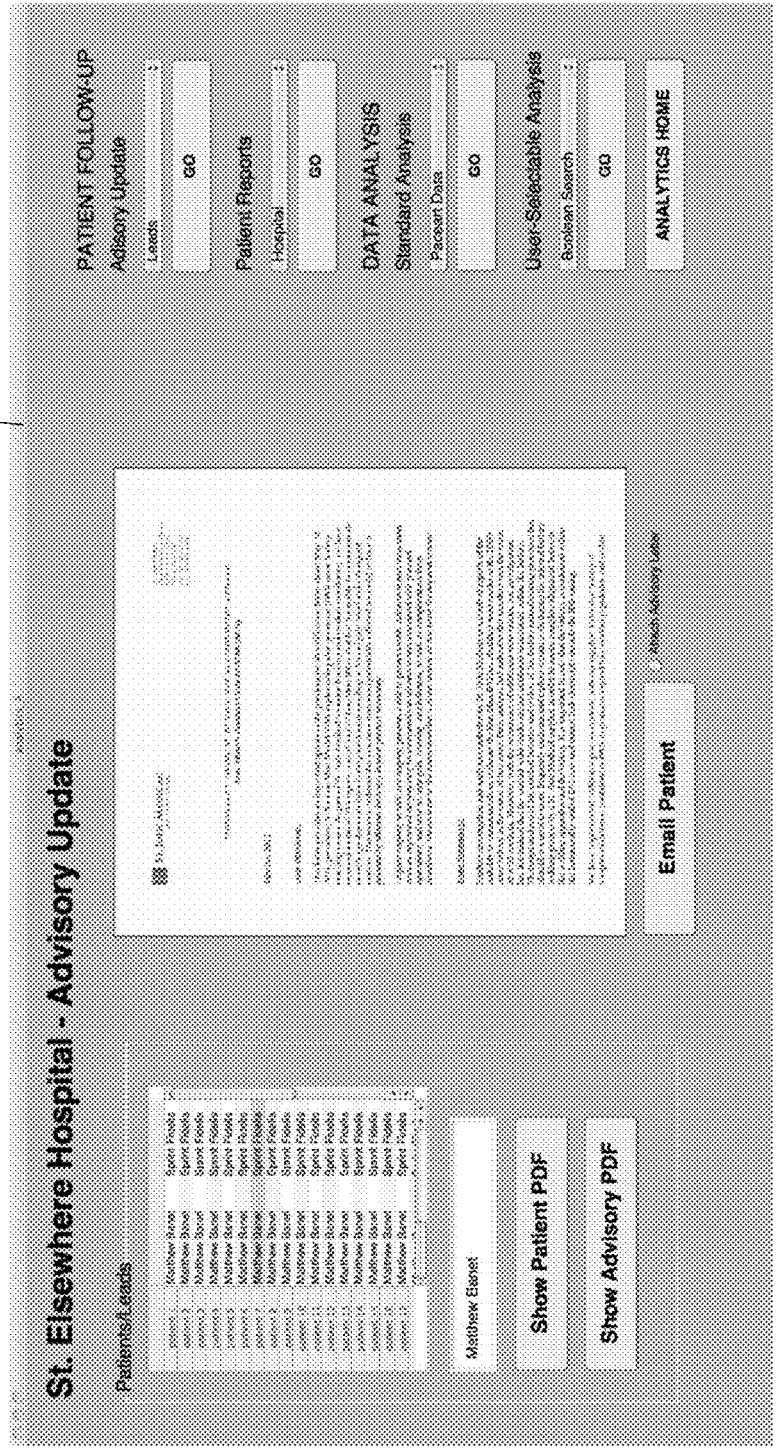
FIG. 6 shows a screenshot from a website of FIG. 4 associated with the data-analytics module that renders a report summarizing an advisory action associated with a ID lead.
Figure 7:
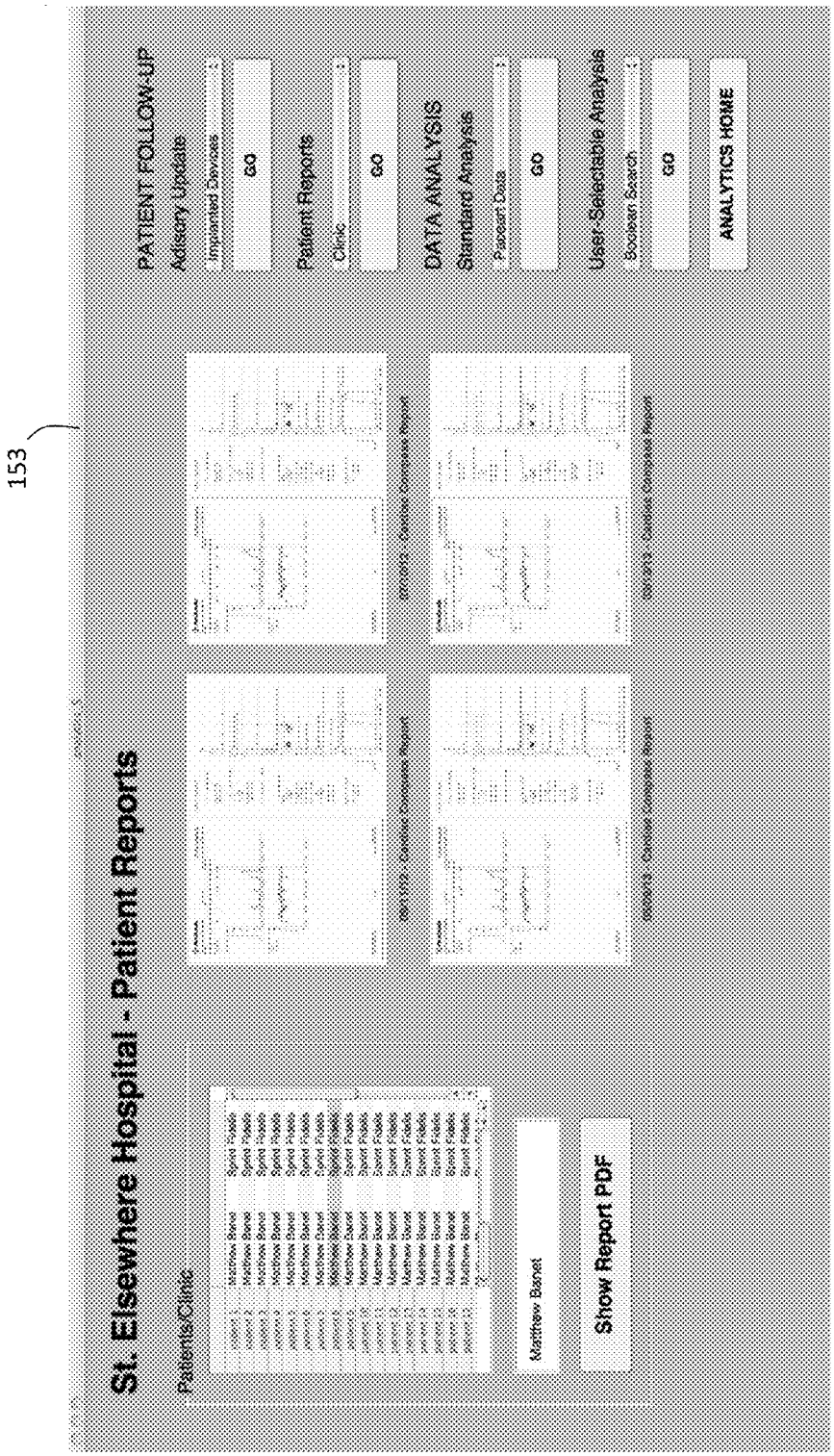
FIG. 7 shows a screenshot from a website of FIG. 4 associated with the data-analytics module that renders a collection of reports summarizing a patient's ID and cardiac response.

The screenshot 151 shown in FIG. 5 is rendered when the user selects 'Leads' in the Patient Follow-Up section on the screenshot's right-hand side, and then clicks the 'Go' button. Doing this allows the clinician to enter a patient's name in a field on the screenshot's left-hand side, and then search for reports associated with the selected patient. For example, the clinician can search for PDF documents that describe a variety of patient-specific data, e.g. clinic visits, IDs associated with the patient, and advisory actions (e.g. recalls) associated with the ID and its ancillary components (e.g. its leads). FIG. 6, for example, shows a screenshot 152 indicating an advisory action for an ID lead (the Sprint Fidelis lead) manufactured by St. Jude Medical. The data-analytics module stores this information in the database, and after rendering it on the screenshot 151, allows the clinician to email it and other information (e.g. reports and other documentation) to the patient, insurance company, or another clinician. In embodiments, the data-analytics module includes software for character recognition that allows content to be extracted from the PDF reports, and then used afterwards in numerical calculations. As shown in FIG. 7, the data-analytics module can render a screenshot 153 that shows multiple reports, all rendered on a single page. As described above, using character-recognition software, the data-analytics module can extract information from these reports and then use it for subsequent calculations.

Figure 8:
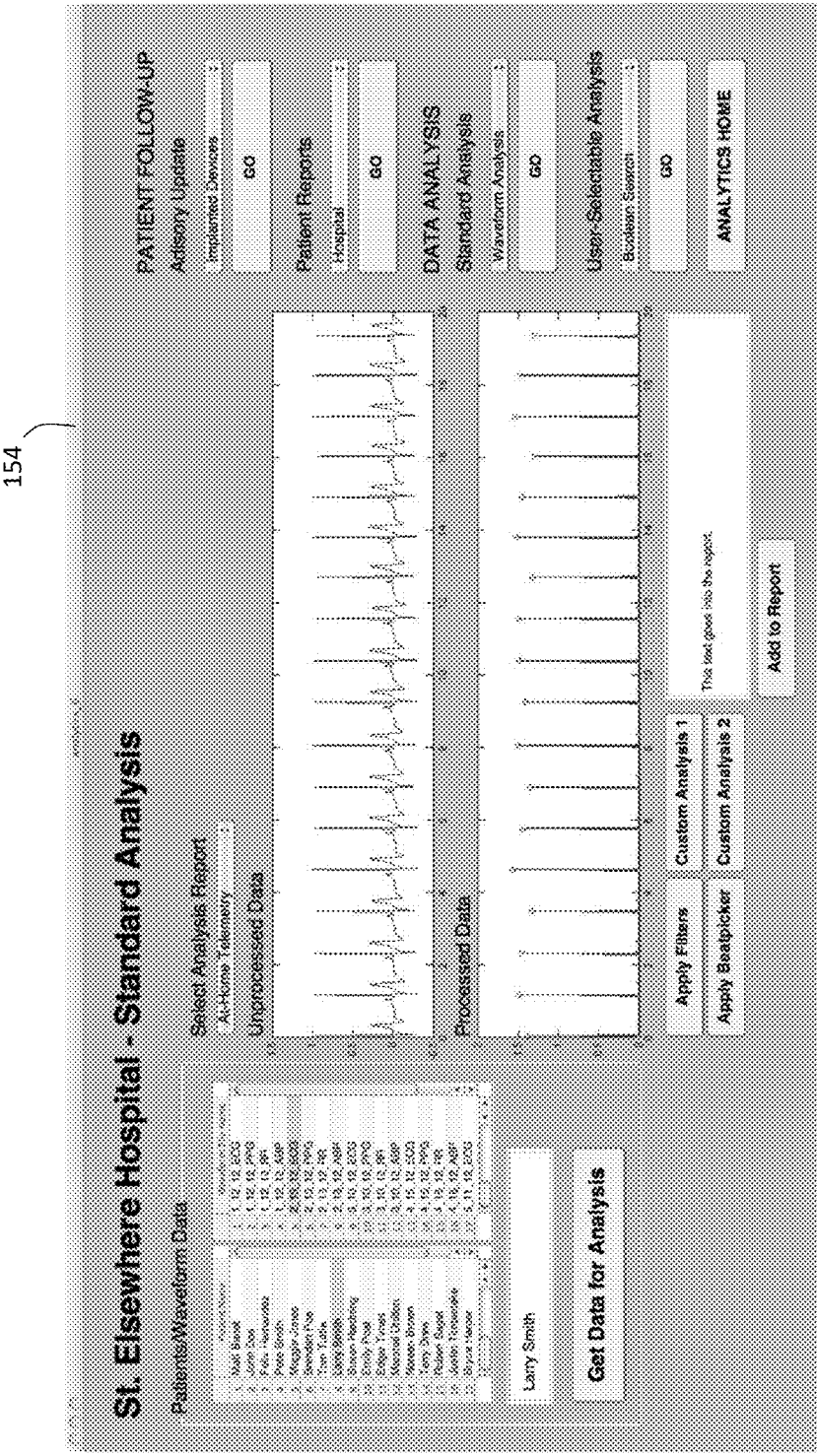
FIG. 8 shows a screenshot from a website associated with the data-analytics module that analyzes ECG waveform data according to a standard analysis.

FIG. 8 shows a screenshot 154 that indicates how the data-analytics module can perform standard, pre-determined analyses. As indicated in the left-hand side of the screen shot, standard fields can be used to select a given patient and then a data field corresponding to the patient. In this case, the data field is an ECG waveform. As shown in the middle section of the screen shot, once selected, the ECG waveform is plotted in a time-dependent form, and can be processed with a variety of pre-determined algorithms, such as digital filters to remove selected high and low-frequency components, a 'beatpicker' that detects a standard QRS complex associated with each heartbeat, and other custom analyses. As shown in the lower plot in the figure, in this example the ECG waveform is sequentially processed with a digital bandpass filter, a derivative filter to remove any slowly varying components, and finally squared to emphasize the QRS complex. The processed waveform is then analyzed with a beatpicker to find each QRS complex, as indicated by the round circle overlapped with each peak. Such custom analyses, for example, can be programmed into the data-analytics module, and then operated when the user clicks the 'Custom Analysis 1' button. In general, any numerical algorithms or other computational techniques can be programmed into the data-analytics module using this technique. Computer languages such as C and Java, or scripted language such as Matlab or PERL, can be used to program in the custom analyses. Once these or any other analyses are performed, the resulting data can be added to a report, along with user-generated text that describes content within the report. The data can also be exported for off-line numerical analysis.

Figure 9:
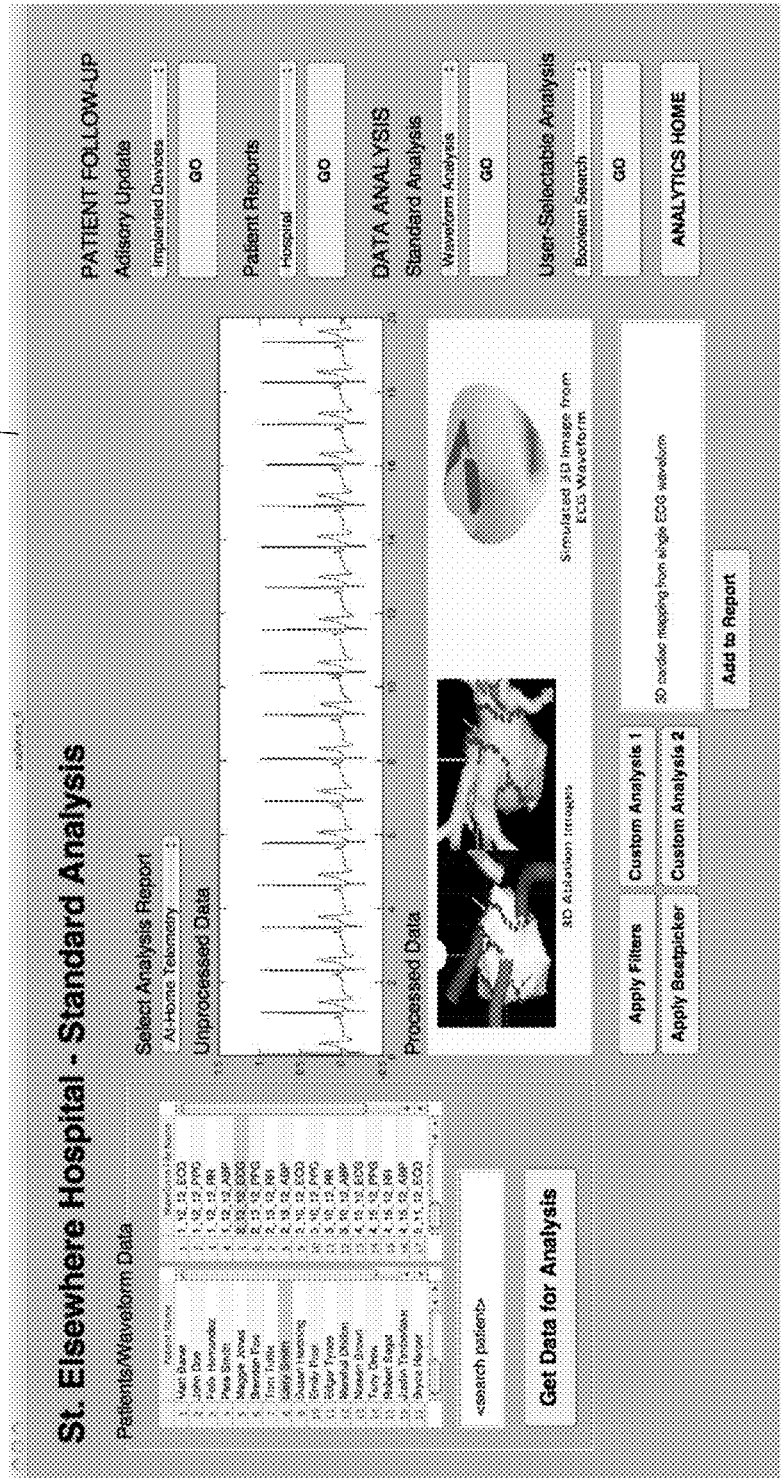
FIG. 9 shows a screenshot from a website of FIG. 4 associated with the data-analytics module that analyzes ECG waveform data according to a custom analysis.

FIG. 9 shows a screenshot 155 that indicates an example of a custom report. Here, data from the EP ablation system (item 165 in FIG. 1; Table 1 shows data from this system) is accessed by the data-analytics system. As shown by the images in the middle of the screenshot 155, the GUI renders data from the EP ablation system as three-dimensional images that show an approximation of the patient's heart and locations of where the ablations actually take place. Next to this image is a secondary image of the patient's heart that graphically indicates conduction pathways therein. Such a simulated image can be approximated from the ECG waveform, as described in U.S. Pat. No. 7,751,875 to Bojovic et al, the contents of which are fully incorporated herein by reference. As an example of a custom analysis, the ablation locations determined from the EP ablation system could be correlated with either the morphology of the patient's ECG waveform or their associated cardiac rhythm, or with a three-dimensional image of the patient's heart simulated from the ECG waveform. Such images may yield information such as damage to the heart or locations of blockages. Other similar correlations are within the scope of this invention.

Figure 10:
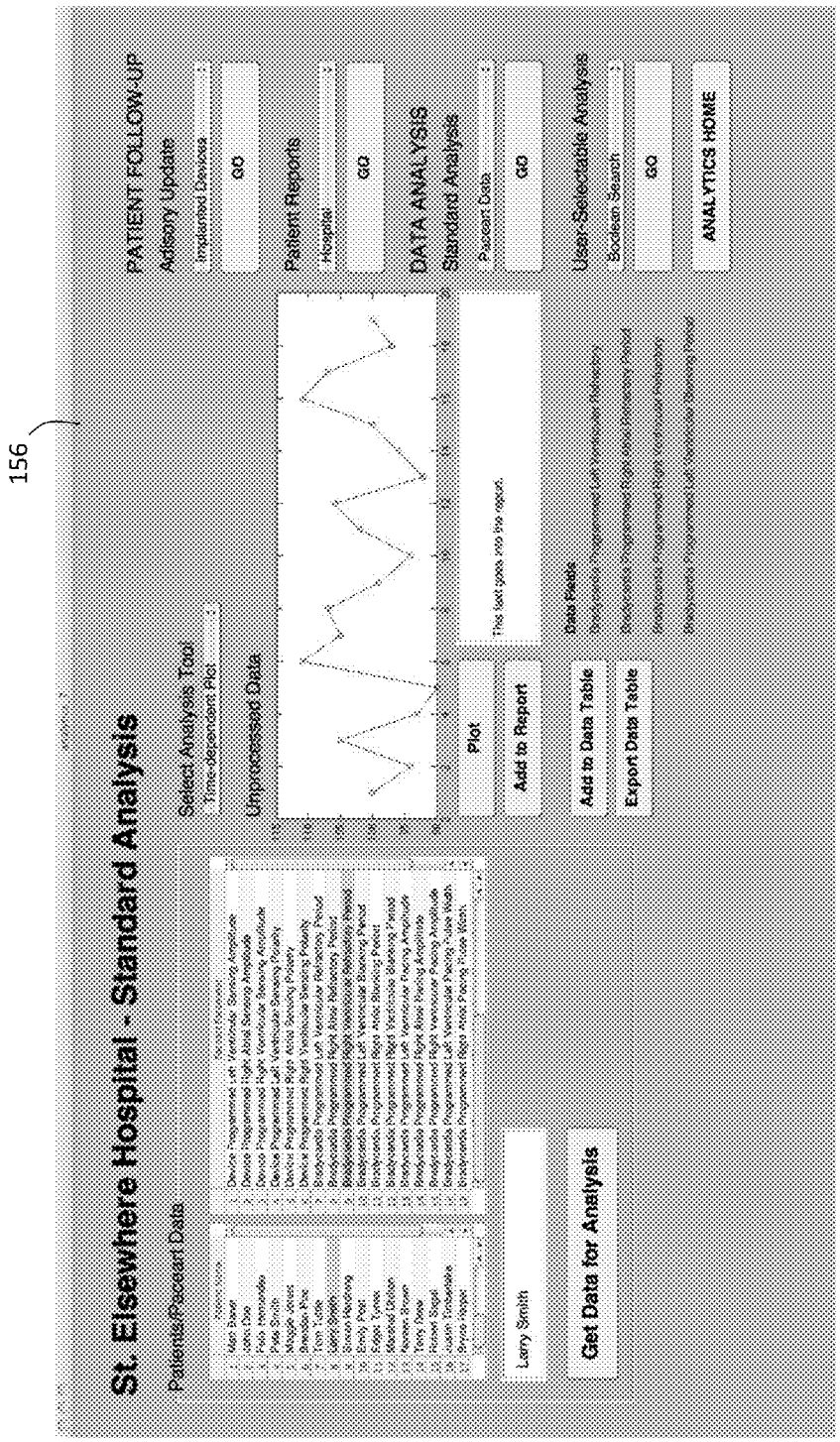
FIG. 10 shows a screenshot from a website of FIG. 4 associated with the data-analytics module that analyzes and plots data from Medtronic's Paceart system.

The data-analytics module also facilitates processing of data generated by the patient's ID and interrogated by a programmer. Alternatively, these data can be secured by accessing the Paceart system described above. Paceart organizes and archives data for IDs across different manufacturers (e.g. Medtronic, St. Jude, Boston Scientific, Biotronix), and serves as a central repository for a patient's arrhythmia information. It provides a gateway through which data flows to a clinic's EHR from programmers that collect data from IDs. As shown in the screen shot 156 in FIG. 10, the data-analytics module allows a user to select a patient and the corresponding data field, generated by the ID, for the patient. In the screenshot 156, the data field is the bradycardia programmed right ventricular refractory period. After they are selected, these data are plotted in the screenshot, with the y-axis representing the value of the refractory period, and the x-axis representing consecutive heartbeats. Each data field generated by the ID and interrogated by the programmer, or alternatively stored in Paceart, can be analyzed in this manner. As described above, more complex analyses are also possible. In general, the data-analytics module allows data fields to be analyzed across patients, devices, hospitals, genders, etc. In this way, for example, the efficacy and performance of the ID can be evaluated using a large number of diverse subjects. This can be done without the expense and time associated with a conventional clinical trial.

Figure 11:
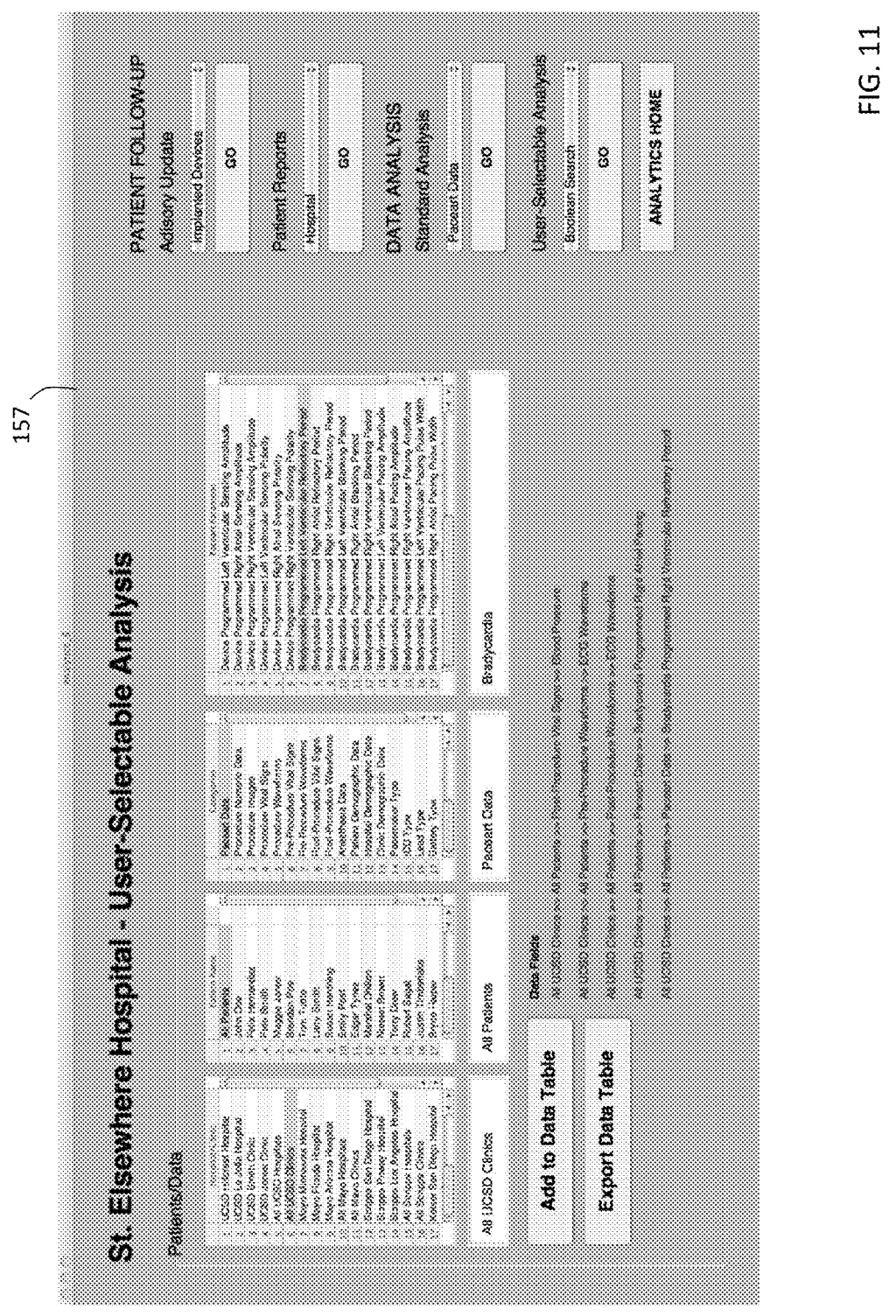

FIG. 11 shows a screenshot 157 that indicates how the data-analytics module can perform sophisticated, user-selectable analyses using data collected as described above. As shown in the figure, the screenshot 157 lists data fields associated with the hospital/clinic, patient, categories of physiological and device-related data, and individual data fields within the particular category. These data sets can be collected from a large number of patients and hospitals, and then grouped together for analysis. Once the data are selected, buttons shown on the screenshot 157 can be used to add the data to a data table, such as one found in a relational database or simple spreadsheet. A similar button can then be used to export the data table, thus allowing the user to analyze it using tools external to the data-analysis module, e.g. custom-written computer programs or tools such as Matlab. In this way, the data-analytics module provides sophisticated sets of data to the user, thus allowing a wide range of analyses. In general, by organizing data in this manner, the data-analytics module functions as a search engine that has access to valuable clinical data normally not available for public consumption. These data are organized and categorized by the data-collection/storage module to ensure their consistency and quality. In this manner, the system allows for sophisticated data analysis normally reserved for expensive and time-consuming clinical trials.

The above-mentioned system can be used to generate clinical analyses and subsequent reports for the clinician that include the following information:

1—physiological information before and after EP treatment

2—ECG waveforms and their various components before and after treatment

3—estimated efficacy of EP treatment

4—the need for EP treatment

5—correlation of patient demographics and EP efficacy

6—correlation of physiological information and EP efficacy

7—correlation between ablation characteristics (e.g. ablation potentials, locations) and stabilization of cardiac rhythm 8—efficacy of ID/leads and stabilization of cardiac rhythm 9—ID battery voltage and stabilization of cardiac rhythm 10—correlation between heart rate variability and occurrence of cardiac trauma (e.g. stroke, myocardial infarction) within well-defined periods of time Other clinical analyses are made possible with the invention described here, and are thus within its scope.

Figure 12:
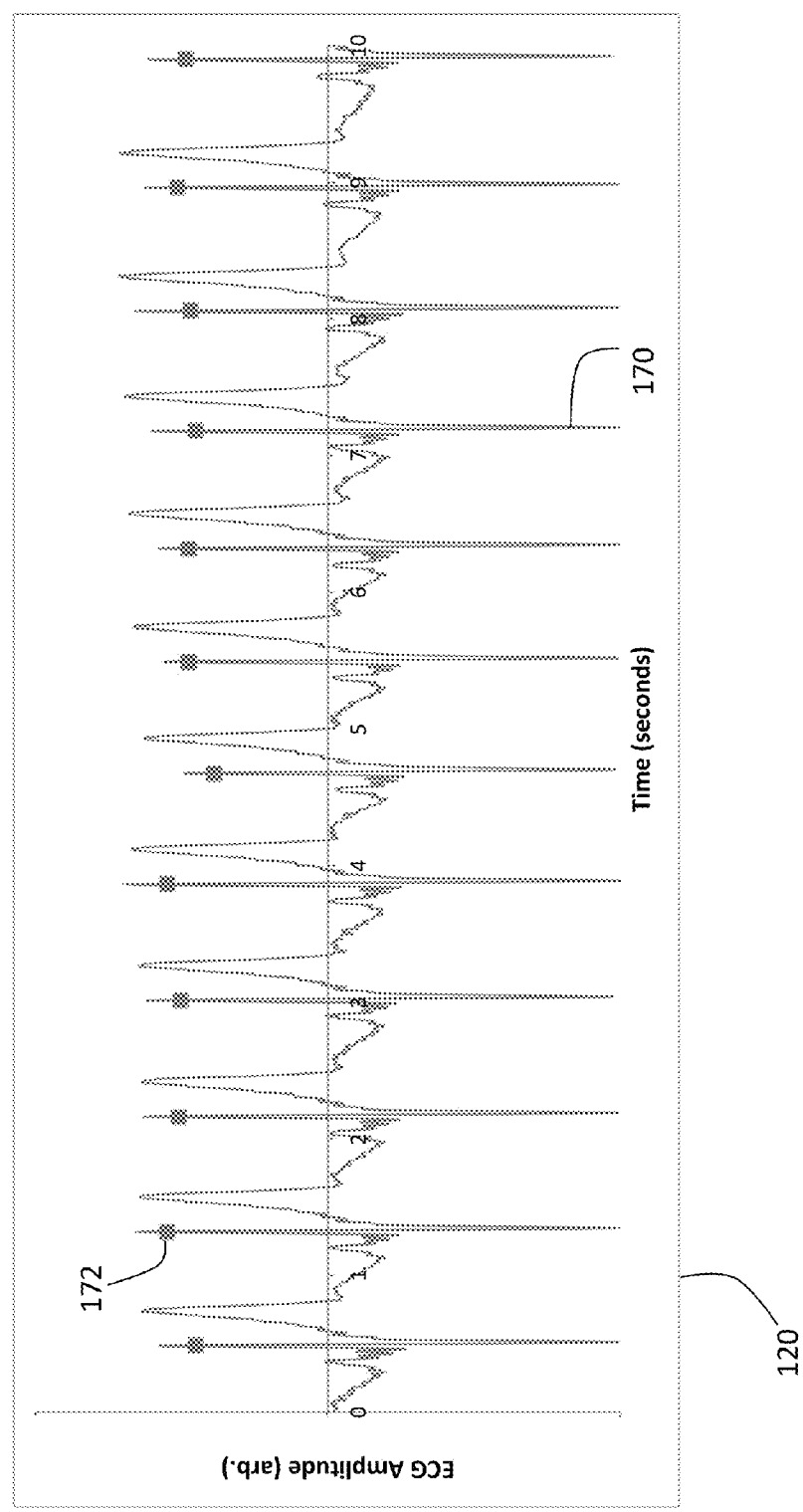
FIG. 12 shows a time-dependent ECG waveform that can be stored in the data-collection/storage module of FIG. 2 and then analyzed with a beat-picking algorithm.

FIG. 12 shows an example of an ECG waveform 150 that is measured from a patient (e.g., before the EP procedure), stored in the database, and then analyzed by an algorithmic-based tool such as that described with reference to FIG. 8 to estimate the patient's cardiac performance. The ECG waveform, which in this case corresponds to a relatively healthy patient, 150 features a collection of equally spaced, time-dependent data points that are defined by a sampling rate of an ECG monitor (such as that shown in FIG. 15), which in this case in 500 Hz. The waveform features a sharply varying peak, called the QRS complex, which indicates initial depolarization of the heart and informally marks the onset of the patient's cardiac cycle. Each heartbeat yields a new QRS complex. After a few hundred milliseconds, a relatively slowly varying feature called the T-wave follows the QRS complex. In general, each patient features a unique ECG waveform from which the algorithmic-based tools can extract important cardiac information. As described above with reference to FIG. 8, a simple algorithmic-based tool called a 'beatpicker' analyzes the ECG waveform 150 to determine the patient's HR and arrhythmia information. In this application, the beatpicker uses an algorithm (called the Pan-Thompkins algorithm) that determines the temporal location of the QRS complex corresponding to each heartbeat. The Pan-Thompkins algorithm typically includes the following steps: i) filtering the ECG waveform to remove any high-frequency noise; ii) taking a mathematical derivative of the waveform; iii) squaring the waveform; iv) signal averaging the waveform; and v) finding the peaks of the waveform processed with steps i)-iv). Locations of the QRS complex from waveforms processed in this manner are shown in the figure by a collection of gray squares 152. Once the collection of QRS complexes is located, the algorithmic-based tool can determine the patient's HR and arrhythmia information using well-known techniques in the art.

The ECG waveform 150 described above is relatively simple, and other than a relatively tall T-wave, lacks any complicated features that challenge conventional beatpickers. However, such features are not uncommon amongst cardiac patients, and thus the beatpicker must be sophisticated enough to analyze them. Moreover, the ECG waveform 172 shown in FIG. 12 only corresponds to a single lead, and thus is relatively unsophisticated and lacks information describing complex cardiovascular performance. Typically, the system according to this invention analyzes multi-lead ECG waveforms 180, such as those shown in FIG. 13. Multi-lead ECG waveforms can contain information from 5, 7, and even 12-lead ECGs. In general, these types of ECG waveforms are required to evaluate the complex cardiovascular performance associated with patients that would most benefit from the present invention.

For example, in embodiments, algorithmic-based tools according to the invention, or software associated with these tools, can also analyze relatively long traces of ECG waveforms (spanning over seconds or minutes) measured before, during, and after the EP procedure to characterize: i) a given patient; ii) the efficacy of the EP procedure applied to that patient; iii) a given patient's need for an EP procedure; or iv) the overall efficacy of the EP procedure as applied to a group of patients. Analysis of the relatively long traces of ECG waveforms in this manner may indicate cardiac conditions such as cardiac bradyarrhythmias, blockage of an artery feeding the heart, acute coronary syndrome, advanced age (fibrosis), inflammation (caused by, e.g., Lyme disease or Chaga's disease), congenital heart disease, ischaemia, genetic cardiac disorders, supraventricular tachycardia such as sinus tachycardia, atrial tachycardia, atrial flutter, atrial fibrillation, junctional tachycardia, AV nodal reentry tachycardia and AV reentrant tachycardia, reentrant tachycardia, Wolff-Parkinson-White (WPW) Syndrome, Lown-Ganong-Levine (LGL) Syndrome, and ventricular tachycardia. Likewise, analysis of these cardiac conditions by analyzing the ECG waveforms may indicate the efficacy of the EP procedure.

Typically, before the algorithmic-based tool deploys the beatpicker, it is analyzed against well-known databases, such as the MIT arrhythmia database or the American Heart Association database, to determine its performance. Beatpickers with a performance of about 95% or greater, as evaluated relative to these standards, are typically categorized as acceptable. Alternatively, as described above, the algorithm-based tools may integrate with commercially available tools for analyzing ECG waveforms, such as those developed and marketed by Mortara.

Figure 13:
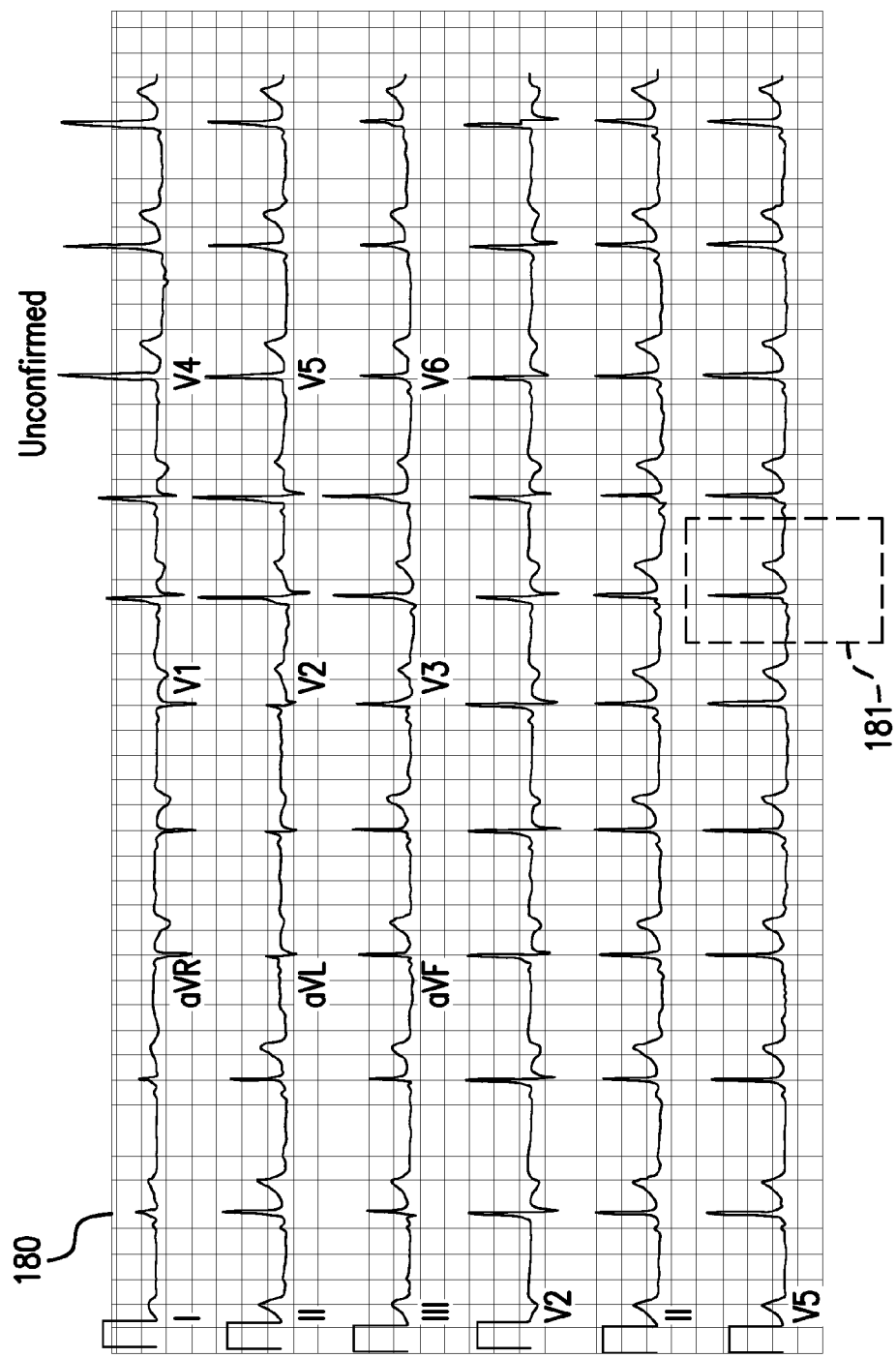
FIG. 13 shows a multi-lead ECG waveform stored in the data-collection/storage module of FIG. 2.
Figure 14:
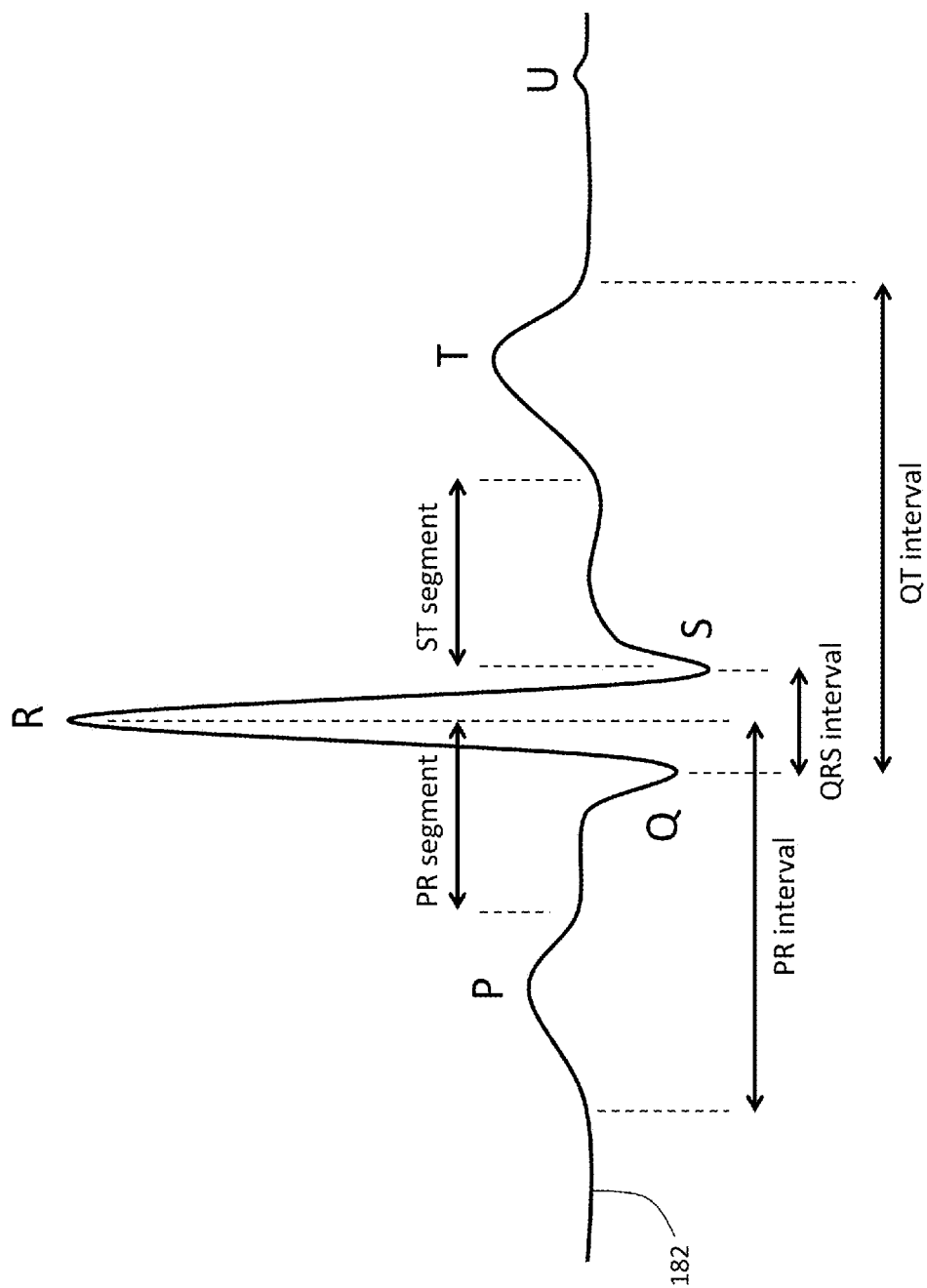
FIG. 14 shows a waveform 'snippet' taken from an ECG waveform in FIG. 13 that indicates various features associated with a patient's cardiac cycle.

FIG. 14 shows a waveform snippet 182 found within the ECG waveform that is shown in the dashed box 181 of FIG. 13. The waveform snippet 182 corresponds to a single heartbeat. Waveform snippets 182 may be collected before, during, and after an EP procedure, and are typically analyzed after they are stored in the database, as described above. Algorithm-based tools within the system, or software components within the algorithm-based tools, may analyze one or more waveform snippets 182 generated by a given patient to predict certain cardiac conditions assigned to that patient. Alternatively, the software may collectively analyze waveform snippets corresponding to large groups of patients to evaluate, e.g., the efficacy of a certain aspect of an EP procedure, or predict how a given EP procedure is likely to affect a given patient.

As shown in the figure, the waveform snippet features the following components: i) a QRS complex; ii) a P-wave; iii) a T-wave; iv) a U-wave; v) a PR interval; vi) a QRS interval; vii) a QT interval; viii) a PR segment; and ix) an ST segment. Algorithmic-based tools within the system, or software associated with the algorithm-based tools, can analyze each of these components and their evolution over time as described above. In particular, algorithmic-based tools that perform numerical fitting or pattern recognition may be deployed to determine the components and their temporal and amplitude characteristics for any given heartbeat recorded by the system. Each component corresponds to a different feature of the patient's cardiac system. For example, the PR interval (which typically has a duration between about 120-200 ms) represents the time from firing of the patient's SA node to the end of the delay of their AV node. A prolonged PR interval, or a PR interval that is inconsistent over time, may indicate blockage of an artery feeding the patient's heart. Alternatively, a shortened or non-existent PR interval may indicate a cardiac condition such as tachycardic, junctional, ectopic, or ventricular rhythms. The QRS interval, which is typically between 40-100 ms, represents the travel time of electrical activity through the patient's ventricles and ventricular depolarization that drives contraction of the heart. QRS intervals that are longer than this, or that feature a 'notch', can indicate aberrant ventricular activity or cardiac rhythms with a ventricular focus.

Variation in the time between subsequent QRS complexes (i.e., the time associated with a given HR) may also indicate a cardiac condition. In general, some variation in this component is normal and indicative of a healthy heart. Little or no variation, which typically becomes more pronounced as the patient ages, or a sudden decrease in variation, may indicate the onset of a cardiac event.

The QT interval, which is typically less than 50% of the total duration of the time associated with the patient's HR, represents the travel time of electrical activity through the patient's ventricles to the end of ventricular repolarization. This parameter varies with HR, and also with age and gender. Prolonged QT intervals represent a prolonged time to cardiac repolarization, and may indicate the onset of ventricular dysrhythmias.

The P-wave, which proceeds the QRS complex of each heartbeat, is typically upright and uniform in shape, and indicates the firing of the SA node and subsequent atrial depolarization; it typically has a width of about 50 ms, and an amplitude that is about 10-20% of the QRS amplitude. P waves that are abnormally wide or notched, or tall and peaked, indicate cardiac conditions such as P-mitrale and P-pulmonale, respectively. The PR segment, which separates this feature from the QRS complex, is typically 120-200 ms in duration, and represents the delay separating the firing of the SA node and ventricular depolarization. A PR segment that gradually increases over time may indicate the onset of damage to the patient's heart. The T-wave, which follows the QRS complex, indicates the onset of ventricular repolarization, and should appear rounded and somewhat symmetrical; the peak of the T-wave is typically relatively close to the wave's end. T-waves that are abnormally tall or 'tented' may indicate cardiac conditions such as hyperkalemia or myorcardial injury. T-waves that are inverted may indicate cardiac conditions such as myocardial ischemia, myocardial infarction, pericarditis, ventricular enlargement, bundle branch block, subarachnoid hemorrhage, and the presence of certain pharmaceutical compounds, such as quinidine or procainamide.

The U-wave, which is somewhat uncommon and when present only about 2-5% of the amplitude of the QRS complex, depicts the last phase of ventricular repolarization. It is typically present with patients undergoing bradycardia, and can be enlarged during cardiac conditions such as hypokalemia, cardiomyopathy, or enlargement of the left ventricle.

Figure 15:
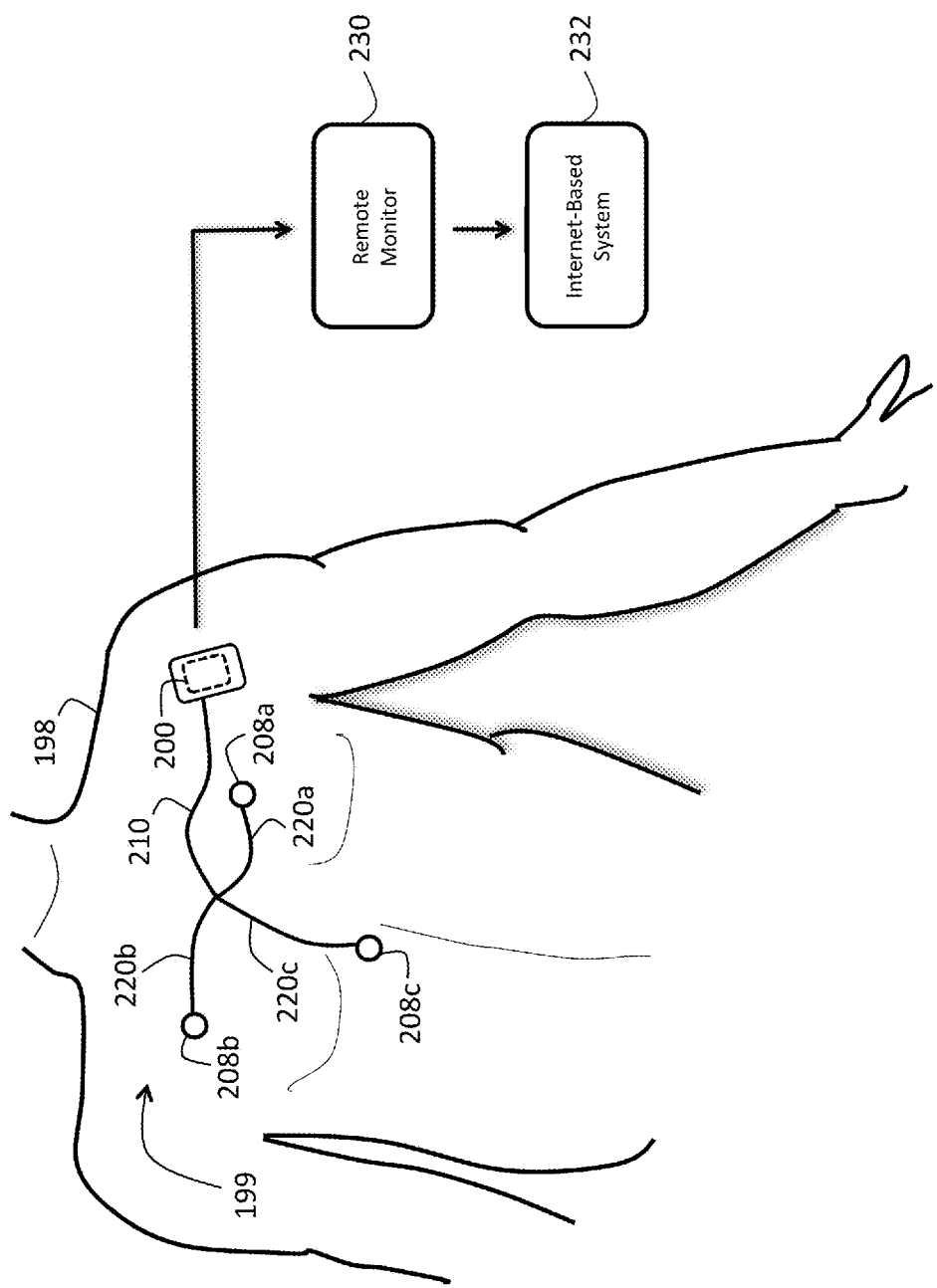
FIG. 15 shows a body-worn ECG monitoring system that measures ECG information and wirelessly transmits it to an Internet-based system associated with the system of FIG. 1.

FIG. 15 shows an example of a body-worn ECG monitoring system 199 according to the invention that continuously monitors ECG waveforms such as those shown in FIG. 12 from an ambulatory patient 198. The body-worn ECG monitoring system 199 features a control unit 200 that features analog electronics for measuring analog ECG waveforms, a processing unit for digitizing the analog ECG waveforms and then processing them as described above to determine HR and arrhythmia information, and a wireless transmitter for sending this information to a remote wireless monitor 230. During use, the control unit 200 connects to a cable 210 that, in turn, connects to a collection of ECG leads 220a-c. FIG. 15 shows a 3-lead system, but it is understood that the present invention could also include 5, 7, and 12-lead ECG systems. Each ECG lead 220a-c terminates with an ECG electrode 208a-c that adheres to the patient's skin and typically connects to the associated lead with a standard snap connector (not shown in the figure). In this case, the 3 ECG electrodes 208a-c are deployed on the patient's chest in a standard 'Einthoven's Triangle' configuration, meaning individual electrodes are attached to the upper left-hand (electrode 208a), upper right-hand (electrode 208b), and lower right-hand (electrode 208c) portions of the patient's torso. During use, the electrodes measure weak analog electrical signals from these locations, and transmit these through their respective leads 220a-c to the processing unit 200, which then processes the signals with the analog circuit to determine one or more analog ECG waveforms. An analog-to-digital converter then digitizes these and avails them to a microprocessor, which runs computer code corresponding to the beatpicker that picks out the appropriate features (e.g. the QRS complex corresponding to each heartbeat) and then analyzes them as described above. The processing unit then wirelessly transmits this and other information (e.g. digitized ECG waveforms) to the remote monitor 230. This system typically includes a computer server that connects through a wired connection to an Internet-based system 232, which in turn integrates with the system according to the invention, as shown schematically in FIG. 1. With this configuration, ECG waveforms measured before, during, and after the EP procedure can be collected and further analyzed by additional algorithm-based tools, such as those described above, to evaluate the patient's cardiac performance.

Other embodiments to the ECG monitoring system 199 shown in FIG. 15, of course, are within the scope of the invention. For example, the system 199 can include additional physiological sensors, such as those that measure other vitals such as BP, RR, SpO2, and body temperature. The sensors can also measure physiological parameters that are not vital signs, such as stroke volume and cardiac output. In general, any physiological parameter (either numerical value or time-dependent waveform) can be measured with systems similar to those described above, and then stored in the database shown in FIG. 1 and analyzed with algorithm-based tools to characterize the patient.

Additionally, the body-worn monitor 199 described with reference to FIG. 15 can take many different forms. For example, the monitor 199 can connect to the remote monitor through a wired connection as opposed to a wireless one. The monitor 199 may also deploy body-worn sensors (e.g. the electrodes 208a-c) in configurations that are different than those described above. The body-worn monitor 199 may also connect directly to the Internet-based system 232, thus bypassing the remote monitor. Different systems with different configurations may also be used to monitor the patient before, during, and after the EP procedure. All of these configurations are within the scope of the invention.

Figure 16:
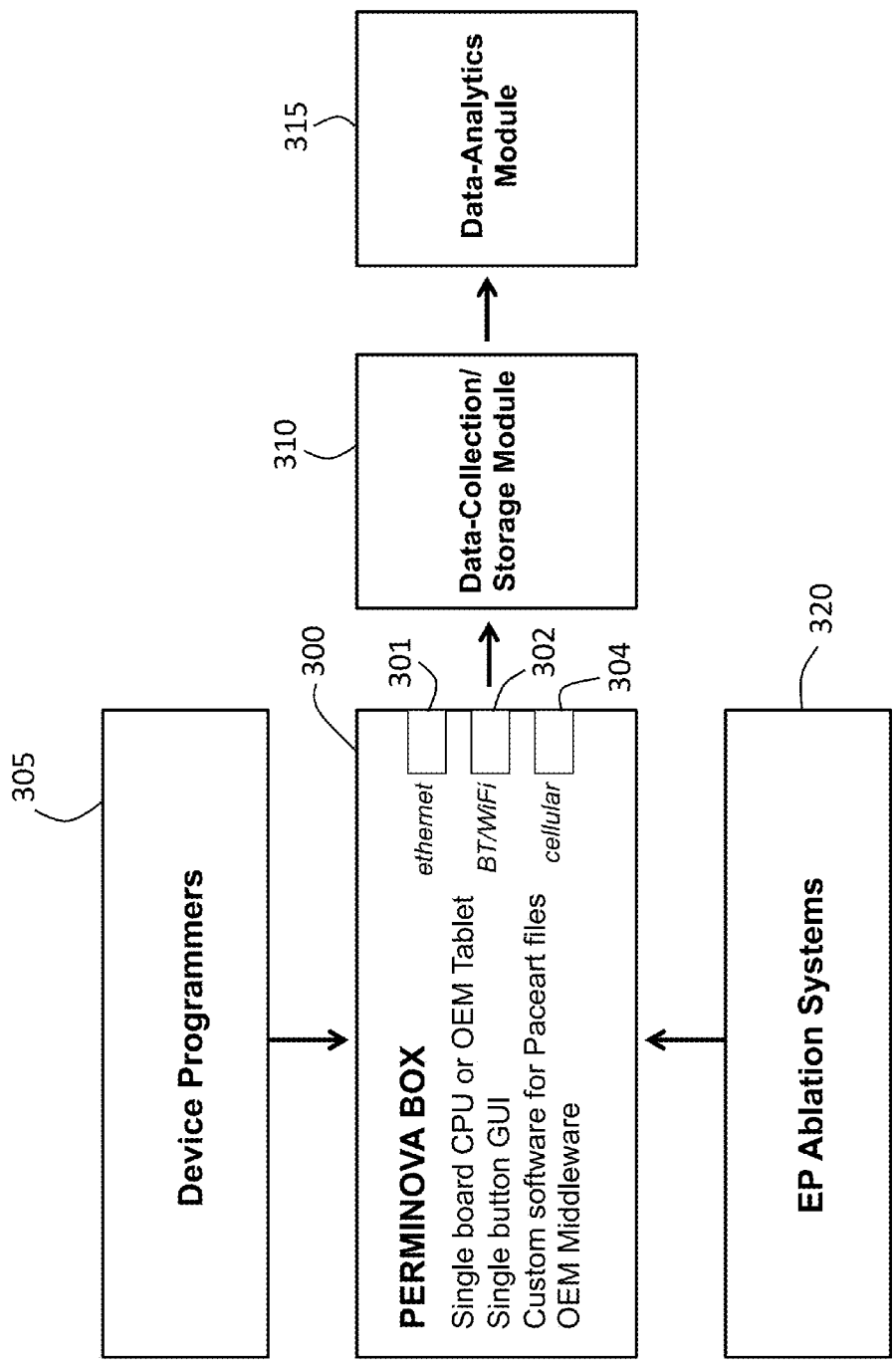
FIG. 16 shows a schematic drawing of a 'Perminova Box' that collects data from device programmers and EP ablations systems, and then forwards these data to a data-collection/storage module, and from there to the a data-analytics module.

In other embodiments, a separate hardware system can be used to collect data from various programmers, and then forward the data into the data-analytics module described above using either wired or wireless technologies. This hardware system can take a variety of forms, and individual hardware systems may be used for each piece of equipment that supplies data to the data collection-storage module. For example, such a hardware system utilizing a wireless system may be particularly useful in hospital environment where it is simply not practical to connect systems through a wired connection. Referring to FIG. 16, such a hardware system, referred to herein as a 'Perminova Box' 300, features interfaces for Ethernet 301, Bluetooth/WiFi 301, or cellular 304 performs this function. During use, the Perminova Box 300 integrates with hardware systems such as device programmers 305 or EP ablation systems 320 through one of the above-mentioned hardware interfaces. It may feature a form factor of a single-board computer, tablet computer, or programmable USB 'dongle' that plugs into an available port on the device programmer 305 and/or the EP ablation system. In embodiments, the programmable USB dongle operates computer code that recognizes when a new file is received, parses the new file to strip out the appropriate data fields, and then transmits these over a wireless connection to the data-collection/storage module. In this way, the Perminova Box 300 can receive data from these devices (typically in the form of XML or PDF files), and in response supply data to the data collection/storage module 310, and eventually to the data-analytics module 315 for processing.

Other embodiments are also within the scope of the invention. For example, other techniques besides the above-described algorithms can be used to analyze data collected with the system. Additionally, processing units and probes for measuring ECG waveforms similar to those described above can be modified and worn on other portions of the patient's body. For example, the ECG-measuring system can be in a patch configuration. Or they can be modified to attach to other sites that yield ECG waveforms, such as the back or arm. In these embodiments the processing unit can be worn in places other than the wrist, such as around the neck (and supported, e.g., by a lanyard) or on the patient's waist (supported, e.g., by a clip that attaches to the patient's belt). In still other embodiments the probe and processing unit are integrated into a single unit. In still other embodiments, the systems for measuring ECG waveforms are implanted or inserted in the patient, e.g. they are part of the ID or EP system.

Systems similar to that described above can also be used for other cardiac procedures conducted in other areas of the hospital, such as the catheterization laboratory, medical clinic, or vascular analysis laboratory. In these applications, data other than HR and ECG waveforms may be analyzed using techniques similar to those described above. Data used in these examples includes medical images (such as those measured using MRI or Doppler/ultrasound), all vital signs, hemodynamic properties such as cardiac output and stroke volume, tissue perfusion, pH, hematocrit, and parameters determined with laboratory studies.

Still other embodiments are within the scope of the following claims.

What is claimed is:

1. A system for determining the presence of cardiac abnormalities in a patient by evaluating T waves from the patient's ECG waveform, comprising:
   (i) a body-worn ECG monitoring system configured to obtain ECG waveforms from the patient comprising:
      at least 2 ECG electrodes,
      a processing unit comprising a first microprocessor, an analog-to-digital converter, and a wireless transmitter, the processing unit operably connected to the ECG electrodes and configured to receive and process electrical signals therefrom to generate one or more digital ECG waveforms, the processing unit further configured to identify one or more features corresponding to one or more heartbeats in the one or more digital ECG waveforms and to wirelessly transmit the one or more features and the digital ECG waveforms;
   (ii) a computer system comprising:
      a database stored on a non-transitory computer-readable storage medium, the database comprising a set of data fields collected from a plurality of individuals, with each data field in the set corresponding to an individual within the plurality of individuals and including a T wave extracted from an ECG waveform obtained from the individual and a parameter indicating the presence of a cardiac abnormality in the individual, and
      a second microprocessor operably connected to the processing unit to receive the one or more features and the one or more digital ECG waveforms wirelessly transmitted by the processing unit, and operably connected to the non-transitory computer-readable storage medium to access the database to store the one or more features and the one or more digital ECG waveforms in a data field corresponding to the patient;
      wherein the second microprocessor performs an ECG-analysis algorithm that processes the one or more ECG waveforms to extract therefrom a set of parameters corresponding to the T wave in the one or more heartbeats,
      wherein the second microprocessor performs an averaging algorithm by processing a plurality of data fields, each data field corresponding to an individual within the plurality of individuals to determine an average correlation factor mapping the parameters corresponding to the T wave to the parameter indicating the presence of a cardiac abnormality, and
      wherein the second microprocessor performs a correlation algorithm configured to evaluate the presence of a cardiac abnormality in the patient by comparing the set of parameters corresponding to the T wave in the one or more heartbeats to the average correlation factor to estimate a new parameter indicating the presence of a cardiac abnormality in the patient, and to store the new parameter in the data field corresponding to the patient.

2. The system of claim 1, wherein the ECG-analysis algorithm is further configured to process the ECG waveform to determine the temporal location of the T wave.

3. The system of claim 1, wherein the ECG-analysis algorithm is further configured to process the ECG waveform to determine the amplitude of the T wave.

4. The system of claim 3, wherein the average correlation factor correlates an amplitude of the T wave to the presence of a cardiac abnormality in the patient.

5. The system of claim 4, wherein the correlation algorithm is further configured to determine the presence of a cardiac abnormality in the patient when the amplitude of the T wave is less than a baseline of the ECG waveform.

6. The system of claim 5, wherein the correlation algorithm is further configured to determine the presence of at least one of myocardial ischemia, myocardial infarction, pericarditis, ventricular enlargement, bundle branch block, subarachnoid hemorrhage when the amplitude of the T wave is less than a baseline of the ECG waveform.

7. The system of claim 5, wherein the correlation algorithm is further configured to determine the presence of a cardiac abnormality in the patient when the amplitude of the T wave is inverted.

8. The system of claim 5, wherein the correlation algorithm is further configured to determine the presence of at least one of myocardial ischemia, myocardial infarction, pericarditis, ventricular enlargement, bundle branch block, and subarachnoid hemorrhage when the amplitude of the T wave is inverted.

9. The system of claim 1, wherein the database, ECG-analysis algorithm, averaging algorithm, and correlation algorithm are comprised by an Internet-accessible system.

10. The system of claim 9, wherein the Internet-accessible system further comprises a graphical user interface (GUI).

11. The system of claim 10, wherein the GUI comprises a webpage that displays the new parameter indicating the presence of at least one of myocardial ischemia, myocardial infarction, pericarditis, ventricular enlargement, bundle branch block, and subarachnoid hemorrhage.

12. The system of claim 1, wherein the ECG-measuring system comprises an ECG circuit configured to be worn on the patient's body, and a transmitting circuit configured to transmit a numerical representation of the ECG waveform to the database.

13. The system of claim 12, wherein the transmitting circuit is configured to transmit the numerical representation of the ECG waveform to an Ethernet port, which then transmits the numerical representation of the ECG waveform to an IP address associated with the database.

14. The system of claim 12, wherein the transmitting circuit is configured to transmit the numerical representation of the ECG waveform to a mobile device, which then transmits the numerical representation of the ECG waveform to an IP address associated with the database.

15. A system for evaluating a presence of at least one of myocardial ischemia, myocardial infarction, pericarditis, ventricular enlargement, bundle branch block, and subarachnoid hemorrhage in a patient, comprising:
(i) a body-worn ECG monitoring system comprising:
at least 3 ECG electrodes,
a processing unit comprising a first microprocessor, an analog-to-digital converter, and a wireless transmitter, the processing unit operably connected to the ECG electrodes and configured to receive and process electrical signals therefrom to generate one or more digital ECG waveforms, the processing unit further configured to identify one or more features corresponding to each heartbeat in the one or more digital ECG waveforms and to wirelessly transmit the one or more features and the digital ECG waveforms;
(ii) a computer system comprising:
a database stored on a non-transitory computer-readable storage medium, the database comprising a set of data fields collected from a plurality of individuals, with each data field in the set corresponding to an individual within the plurality of individuals and including a T wave extracted from an ECG waveform obtained from the individual and a parameter indicating the presence of at least one of myocardial ischemia, myocardial infarction, pericarditis, ventricular enlargement, bundle branch block, and subarachnoid hemorrhage in the individual, and
a second microprocessor operably connected to the processing unit to receive the one or more features and the one or more digital ECG waveforms wirelessly transmitted by the processing unit, and operably connected to the non-transitory computer-readable storage medium to access the database to store the one or more features and the one or more digital ECG waveforms in a data field corresponding to the patient;
wherein the second microprocessor performs an ECG-analysis algorithm that processes the one or more ECG waveforms to extract therefrom a set of parameters corresponding to the T wave in the one or more heartbeats,
wherein the second microprocessor performs an averaging algorithm by processing a plurality of data fields, each data field corresponding to an individual within the plurality of individuals to determine an average correlation factor mapping the set parameters corresponding to the T wave to the parameter indicating at least one of myocardial ischemia, myocardial infarction, pericarditis, ventricular enlargement, bundle branch block, and subarachnoid hemorrhage, and
wherein the second microprocessor performs a correlation algorithm configured to evaluate the presence of at least one of myocardial ischemia, myocardial infarction, pericarditis, ventricular enlargement, bundle branch block, and subarachnoid hemorrhage in the patient by comparing the set of parameters corresponding to the T wave in the one or more heartbeats to the average correlation factor to estimate a new parameter indicating the presence of at least one of myocardial ischemia, myocardial infarction, pericarditis, ventricular enlargement, bundle branch block, and subarachnoid hemorrhage, and to store the new parameter in the data field corresponding to the patient.

* * * * *